United States Patent [19]
Shiraishi et al.

[11] Patent Number: 5,891,895
[45] Date of Patent: Apr. 6, 1999

[54] HYDROXYPYRIDINE DERIVATIVES THEIR PRODUCTION AND USE

[75] Inventors: Mitsuru Shiraishi, Amagasaki; Tsuyoshi Maekawa, Ikoma-gun; Toshifumi Watanabe, Kawachinagno, all of Japan

[73] Assignee: Takeda Chemical Industries, Ltd., Osaka, Japan

[21] Appl. No.: 834,123

[22] Filed: Apr. 14, 1997

[30] Foreign Application Priority Data

Apr. 15, 1996 [JP] Japan .................................. 8-092904

[51] Int. Cl.$^6$ ...................... A61K 31/44; C07D 213/53; C07D 213/89
[52] U.S. Cl. ...................... 514/345; 514/348; 514/351; 546/296; 546/300
[58] Field of Search .................... 546/296, 300; 514/345, 348, 351

[56] References Cited

U.S. PATENT DOCUMENTS

| | | | |
|---|---|---|---|
| 3,930,672 | 1/1976 | Ozutsumi et al. | 503/222 |
| 4,297,359 | 10/1981 | van Zorge | 514/336 |
| 4,798,841 | 1/1989 | Downs et al. | 514/357 |
| 4,971,985 | 11/1990 | Otsuka et al. | 514/357 |
| 5,039,685 | 8/1991 | Knutsen et al. | 514/326 |
| 5,071,860 | 12/1991 | Koenigswinter et al. | 514/332 |
| 5,086,051 | 2/1992 | James et al. | 514/228.2 |

FOREIGN PATENT DOCUMENTS

| | | |
|---|---|---|
| 0 623 597 A1 | 11/1994 | European Pat. Off. . |
| 4-99767 | 3/1992 | Japan . |
| 350461 | 1/1961 | Switzerland . |
| 1 510 977 | 8/1974 | United Kingdom . |
| 93/21146 | 10/1993 | WIPO . |

OTHER PUBLICATIONS

The Merck Index, Eleventh Edition, p. 1234, Compound No. 7782 'Progabide', 1989.

Cameron et al., Chemical Abstracts, vol. 97, No. 25, 1982, Abstract No. 215955d.

(List continued on next page.)

Primary Examiner—Alan L. Rotman
Attorney, Agent, or Firm—Wenderoth, Lind & Ponack, L.L.P.

[57] ABSTRACT

Hydroxypyridine derivatives of the formula wherein $R^1$ is a branched $C_{3-8}$ alkyl group or a $C_{3-8}$ cycloalkyl group, each of which may be substituted;

$R^2$ is a halogen atom, a $C_{1-4}$ alkyl group or a $C_{1-4}$ alkoxy group;

X is an oxygen atom or $NR^3$ in which $R^3$ is a hydrogen atom or a $C_{1-4}$ alkyl group;

$R^4$, $R^5$ and $R^6$ are independently (1) a hydrogen atom, (2) a halogen atom, (3) a cyano group, (4) a nitro group, (5) a $C_{1-4}$ acyl group, (6) a $C_{1-4}$ alkoxy group which may be substituted with halogen, (7) a $C_{1-4}$ alkyl group which may be substituted with halogen or (8) a mercapto group which may be substituted with a $C_{1-4}$ alkyl group;

m is 0 to 3; and n is 0 or 1;

provided that all of $R^4$, $R^5$ and $R^6$ are not hydrogen atom, or a salt thereof, which have potassium channel opening activity and are useful as therapeutic agents of cardiovascular diseases such as angina pectoris, hypertension, etc.

24 Claims, 4 Drawing Sheets

OTHER PUBLICATIONS

Hodogaya Chemical Co., Chemical Abstracts, vol. 97, No. 24, 1982, Abstract No. 199542j.

Duennenberger et al., Chemical Abstracts, vol. 55, No. 20, 1961, Abstract No. 19747i.

Chemical Abstracts, vol. 125, No. 16, 1996, Abstract No. 204523g.

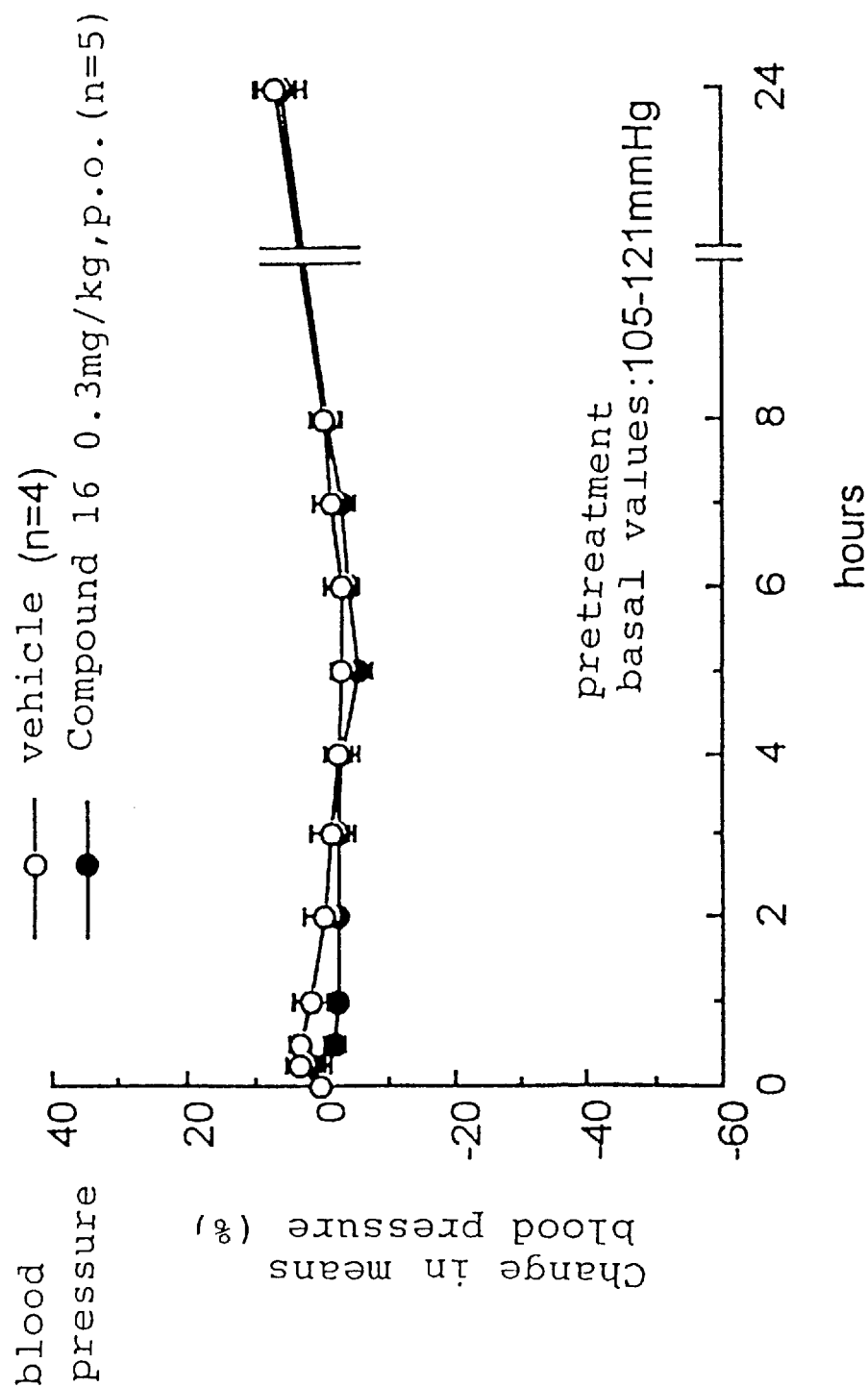

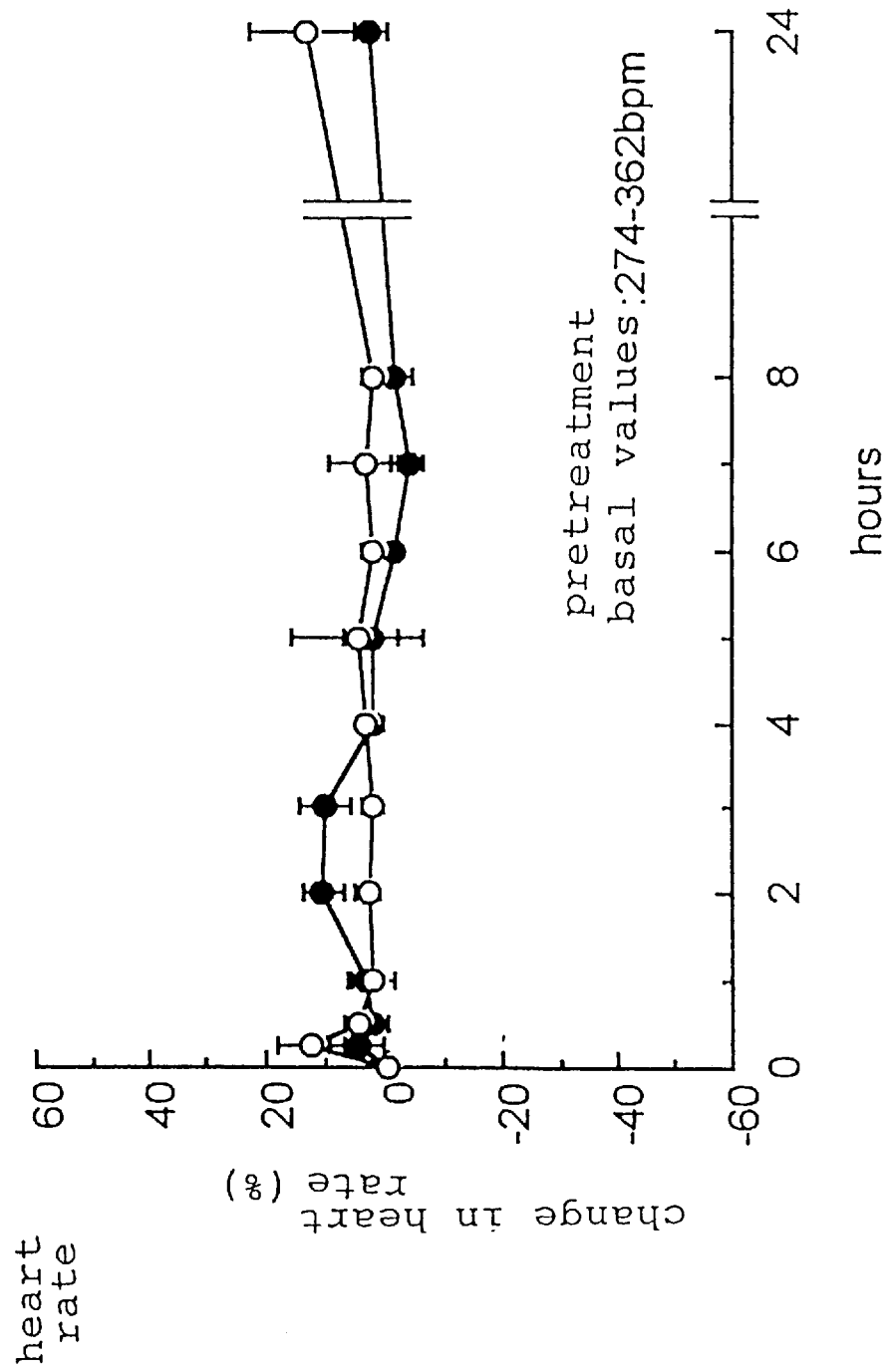

HYDROXYPYRIDINE DERIVATIVES THEIR PRODUCTION AND USE

BACKGROUND OF THE INVENTION

1. Field of the Invention

This invention relates to novel 3-hydroxypyridine derivatives useful as medicines, a method of producing them and pharmaceutical compositions containing them.

The novel 3-hydroxypyridine derivatives of this invention have smooth muscle relaxation activities, coronary blood flow increasing activities, antihypertensive activities, ischemic cardiomuscular protective activities and lipometabolic ameliorative activities, and have therapeutic (treating) and prophylactic (preventing) effects against, for example, cardiovascular diseases such as angina pectoris, cardiac infarction, cardiac insufficiency, arrhythmia and hypertension; respiratory diseases such as asthma; cerebral diseases such as cerebrovascular contraction, apoplectic stroke and epilepsy; enuresis; peptic ulcer; hypersensitive intestinal disturbances; and alopecia.

2. Description of Related Art

Recently, a new type of drugs called a potassium channel opener exhibiting smooth muscle relaxation activities by opening (activating) the potassium channel has attracted attention. For example, chroman-3-ol derivatives which have the potassium channel opening (activating) activity and exhibit antihypertensive activity on spontaneous hypertensive rats are disclosed in JPA S58(1983)-67683 corresponding to EPA 76075, J. Med. Chem., 29, pp. 2194–2201 (1986) and Br. J. Pharmac. 88, pp. 103–111 (1986). In U.S. Pat. No. 4,057,636, cyanoguanidine derivatives having antihypertensive activities is disclosed. However, 3-hydroxy pyridine derivatives having potassium channel opening activities have not been known yet.

SUMMARY OF THE INVENTION

The present invention is to provide novel 3-hydroxypyridine derivatives and their salts which have smooth muscle relaxation activities, coronary blood flow increasing activities, antihypertensive activities, ischemic cardiomuscular protective activities and lipometabolic ameliorative activities, and have therapeutic and prophylactic activities against cardiovascular diseases such as angina pectoris, arrhythmia, cardiac insufficiency, cardiac infarction and hypertension, cerebral diseases such as cerebrovascular contraction, apoplectic stroke and epilepsia, asthma and urinary incontinence, and, besides, are useful for topical therapy of alopecia.

The present inventors studied intensively on benzoylpyridine derivatives, and, as the result, synthesized new 3-hydroxypyridine derivatives represented by formula [I]

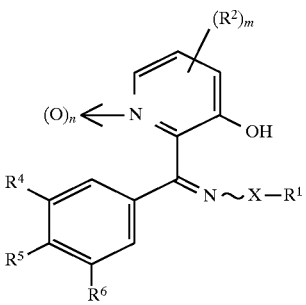

wherein $R^1$ is a branched $C_{3-8}$ alkyl group or a $C_{3-8}$ cycloalkyl group, each of which may be substituted;

$R^2$ is a halogen atom, a $C_{1-4}$ alkyl group or a $C_{1-4}$ alkoxy group;

X is an oxygen atom or $NR^3$ in which $R^3$ is a hydrogen atom or a $C_{1-4}$ alkyl group;

$R^4$, $R^5$ and $R^6$ are independently (1) a hydrogen atom, (2) a halogen atom, (3) a cyano group, (4) a nitro group, (5) a $C_{1-4}$ acyl group, (6) a $C_{1-4}$ alkoxy group which may be substituted with halogen, (7) a $C_{1-4}$ alkyl group which may be substituted with halogen or (8) a mercapto group which may be substituted with a $C_{1-4}$ alkyl group;

m is 0 to 3; and n is 0 or 1;

provided that all of $R^4$, $R^5$ and $R^6$ are not hydrogen atom, or a salt thereof, (hereinafter simply called the compound [I]) having the chemical structure characterized by having hydroxyl group at the 3-position of the pyridyl group, and found that this compound [I] has, unexpectedly, excellent potassium channel opening activities. Based on this finding, the present invention was accomplished.

BRIEF EXPLANATION OF DRAWINGS

FIG. 2 shows effects of 3-hydroxypyridine derivatives (Compound [I] as mentioned hereinafter) on the blood pressure and heart rate in WKY (Wistar-Kyoto rats).

DETAILED DESCRIPTION OF THE INVENTION

Figure 1A:
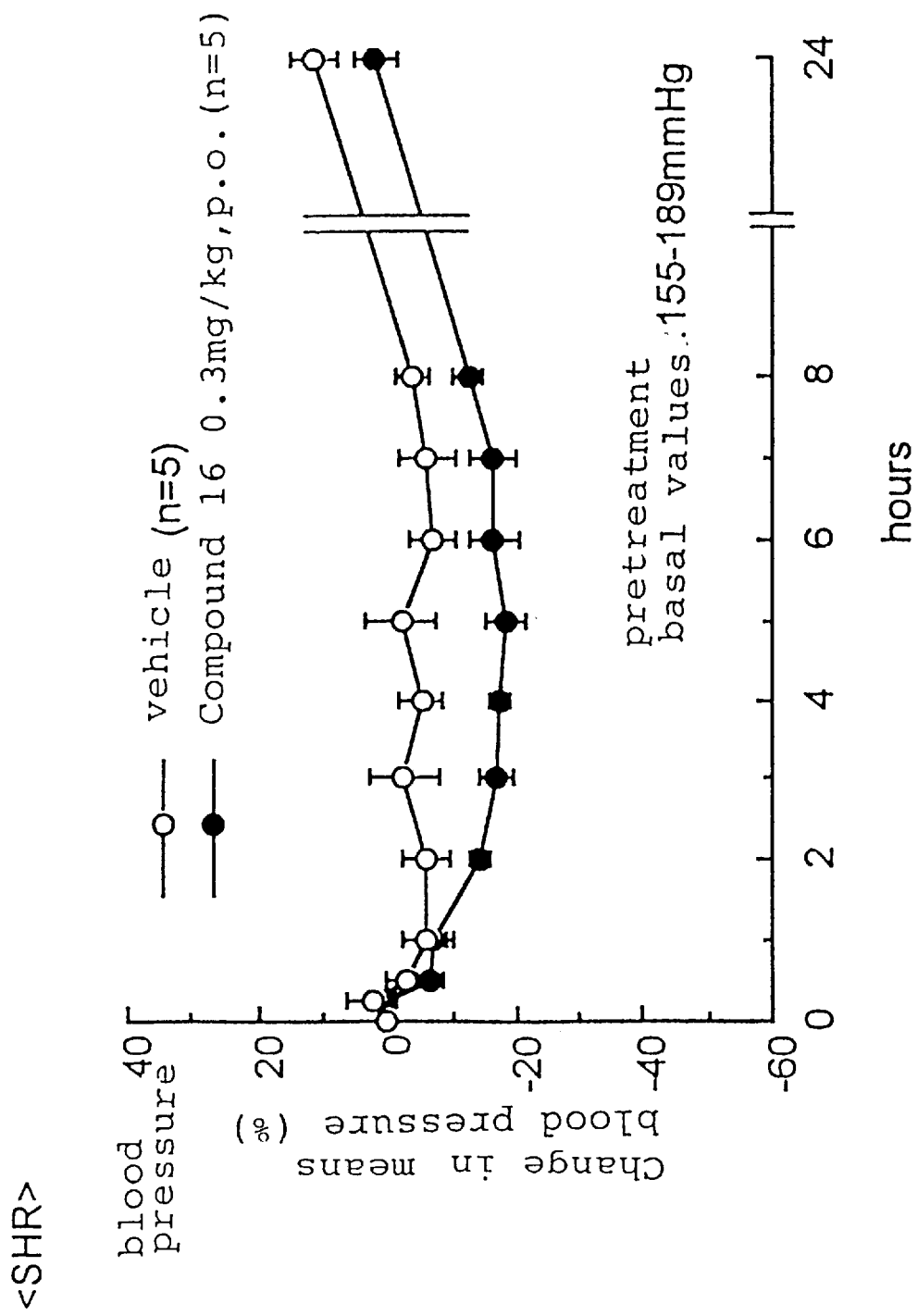
FIG. 1 shows effects of 3-hydroxypyridine derivatives (Compound [I] as mentioned hereinafter) on the blood pressure and heart rate in SHR (spontaneously hypertensive rats).

More specially, the present invention relates to:

1) the compound [I],
2) a compound of the above 1), wherein $R^1$ is a branched $C_{3-8}$ alkyl group or a $C_{3-8}$ cycloalkyl group, each of which may be substituted with 1 to 3 groups selected from (i) a halogen atom, (ii) a halogeno-$C_{1-4}$ alkyl group, (iii) a $C_{1-4}$ alkoxy group, (iv) a phenyl group which may be substituted with 1 to 3 groups selected from a $C_{1-4}$ alkyl group, a $C_{1-4}$ alkoxy group, a hydroxy group, a nitro group, a halogen atom, a halogeno $C_{1-4}$ alkyl group, a cyano group and a halogeno-$C_{1-4}$ alkoxy group, (v) $CO_2R^7$ in which $R^7$ is a hydrogen atom or a $C_{1-4}$ alkyl group and (vi) $CH_2OR^8$ in which $R^8$ is a hydrogen atom or a $C_{1-4}$ alkyl group,
3) a compound of the above 1), wherein $R^4$, $R^5$ and $R^6$ are independently a hydrogen atom, a halogen atom, a cyano group, a nitro group or a halogeno $C_{1-4}$ alkyl group, 4) a compound of the above 1), wherein $R^4$ and $R^5$ are a halogen atom and $R^6$ is a hydrogen atom, 5) a compound of the above 1), wherein $R^1$ is a branched $C_{3-8}$ alkyl group or a $C_{3-8}$ cycloalkyl group, each of which may be substituted with (i) halogen, (ii) $CO_2R^7$ in which $R^7$ is hydrogen or $C_{1-4}$ alkyl or (iii) $CH_2OR^8$ in which $R^8$ is hydrogen or $C_{1-4}$ alkyl, 6) a compound of the above 1), wherein $R^1$ is a $C_{3-8}$ alkyl group branched at α-position, 7) a compound of the above 1), wherein $R^1$ is a t-butyl group, 8) a compound of the above 1), wherein m is 0, 9) a compound of the above 1), wherein n is 0, 10) a compound of the above 1), wherein X is an oxygen atom, 11) a compound of the above 1), which is a Z isomer, 12) a compound of the above 1), wherein $R^1$ is a branched $C_{3-8}$ alkyl group; X is an oxygen atom or NH; $R^4$, $R^5$ and $R^6$ are independently a hydrogen atom, a halogen atom, a cyano group, a nitro group or a halogeno $C_{1-4}$ alkyl group; m is 0; and n is 0 or 1, 13) a compound of the above 1), which is (Z)-2-[3-bromo-α-(t-butoxyimino)benzyl]-3-hydroxypyridine or a salt thereof, 14) a compound of the above 1), which is (Z)-2-[α-(t-butoxyimino)-3,5-dichlorobenzyl]-3-hydroxypyridine or a salt thereof, 15) a compound of the above 1), which is (Z)-2-[3-bromo-α-(t-butoxyimino)-4-fluorobenzyl]-3-hydroxypyridine or a salt thereof, 16) a compound of the above 1), which is (Z)-2-[α-(t-butoxyimino)-3-trifluoromethylbenzyl]-3-hydroxypyridine or a salt thereof, 17) a compound of the above 1), which is (Z)-2-[α-(t-butoxyimino)-3-nitrobenzyl]-3-hydroxypyridine or a salt thereof, 18) a compound of the above 1), which is (Z)-2-[3-bromo-α-(t-butoxyimino)-4-fluorobenzyl]-3-hydroxypyridine N-oxide or a salt thereof, 19) a pharmaceutical composition which comprises a compound of the above 1), in admixture with a pharmaceutically acceptable carrier or excipient, 20) a pharmaceutical composition for treating or preventing cardiovascular disease, which comprises a compound of the above 1), in admixture with a pharmaceutically acceptable carrier, excipient or diluent, 21) a pharmaceutical composition of the above 20), wherein the cardiovascular disease is angina pectoris, 22) a pharmaceutical composition of the above 20), wherein the cardiovascular disease is hypertension, 23) a process for producing a compound of the above 1) which comprises reacting a compound of the formula

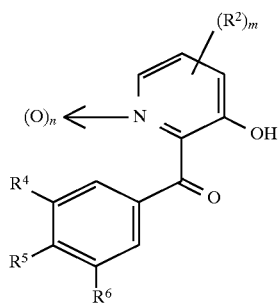

wherein the symbols are as defined in the above 1) or a salt thereof, with a compound of the formula

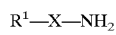

wherein the symbols are as defined in the above 1) or a salt thereof, and so on.

In the above formula [I], $R^1$ is a branched $C_{3-8}$ alkyl group or a $C_{3-8}$ cycloalkyl group, each of which may be substituted.

Examples of the branched $C_{3-8}$ alkyl group represented by $R^1$ include isopropyl, isobutyl, t-butyl, s-butyl, isopentyl, neopentyl, t-pentyl, 1-methylbutyl, 2-methylbutyl, 1,2-dimethylpropyl, 1-ethylpropyl, isohexyl, 1-methylpentyl, 2-methylpentyl, 3-methylpentyl, 1,1-dimethylbutyl, 1,2-dimethylbutyl, 2,2-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl. Among others, t-butyl is more preferred.

Examples of the $C_{3-8}$ cycloalkyl group represented by $R^1$ include cyclopropyl, cyclobutyl, cyclopentyl, and cyclohexyl. Preferable example of $R^1$ is a branched $C_{3-8}$ alkyl group.

Examples of the substituents of the branched $C_{3-8}$ alkyl group or the $C_{3-8}$ cycloalkyl group represented by $R^1$ include 1 to 3 groups selected from (i) a halogen atom (for example, fluorine, chlorine, bromine, iodine), (ii) a halogeno-$C_{1-4}$ alkyl group (for example, $C_{1-4}$ alkyl groups substituted by 1 to 5 halogen atoms such as $CF_3$, $CF_3CF_2$, $CH_2F$ and $CHF_2$), (iii) a $C_{1-4}$ alkoxy group (for example, methoxy, ethoxy, propoxy, isopropoxy, butoxy, isobutoxy, t-butoxy), (iv) a phenyl group which may be substituted with 1 to 3 groups selected from a $C_{1-4}$ alkyl group (for example, methyl, ethyl, propyl, isopropyl, butyl, isobutyl, t-butyl), a $C_{1-4}$ alkoxy group (for example, methoxy, ethoxy, propoxy, isopropoxy, butoxy, isobutoxy, t-butoxy), a hydroxy group, a nitro group, a halogen atom (for example, fluorine, chlorine, bromine, iodine), a halogeno-$C_{1-4}$ alkyl group (for example, $C_{1-4}$ alkyl groups substituted by 1 to 5 halogen atoms such as $CF_3$, $CF_3CF_2$, $CH_2F$ and $CHF_2$), a cyano group and a halogeno-$C_{1-4}$ alkoxy group (for example, $C_{1-4}$ alkoxy groups substituted by 1 to 5 halogen atoms such as $CF_3O$ and $HCF_2O$), (v) $CO_2R^7$ in which $R^7$ is a hydrogen atom or a $C_{1-4}$ alkyl group and (vi) $CH_2OR^8$ in which $R^8$ is a hydrogen atom or a $C_{1-4}$ alkyl group.

Examples of the $C_{1-4}$ alkyl group represented by $R^7$ and $R^8$ include methyl, ethyl, propyl, isopropyl, butyl, isobutyl and t-butyl. Preferable examples of $R^1$ include a branched $C_{3-8}$ alkyl group or a $C_{3-8}$ cycloalkyl group, each of which may be substituted with halogen, $CO_2R^7$ in which $R^7$ is hydrogen or $C_{1-4}$ alkyl, or $CH_2OR^8$ in which $R^8$ is hydrogen or $C_{1-4}$ alkyl. Among others, the branched $C_{3-8}$ alkyl groups are preferred, $C_{3-8}$ alkyl groups branched at α-position are more preferred and the most preferable example is t-butyl.

In the above formula [I], X is an oxygen atom or $NR^3$ in which $R^3$ is a hydrogen atom or a $C_{1-4}$ alkyl group.

Examples of the $C_{1-4}$ alkyl group represented by $R^3$ include methyl, ethyl, propyl, isopropyl, butyl, isobutyl and t-butyl. Preferable example of $R^3$ is a hydrogen atom. Preferable example of X is an oxygen atom.

In the above formula [I], $R^2$ is a halogen atom, a $C_{1-4}$ alkyl group or a $C_{1-4}$ alkoxy group.

Example of the $C_{1-4}$ alkyl group represented by $R^2$ include methyl, ethyl, propyl, isopropyl, butyl, isobutyl and t-butyl. Examples of the $C_{1-4}$ alkoxy group represented by $R^2$ include methoxy, ethoxy, propoxy, isopropoxy, butoxy, isobutoxy and t-butoxy.

In the above formula [I], m is 0 to 3. Preferable example of m is 0.

In the above formula [I], n is 0 or 1. Preferable example of n is 0.

In the above formula [I], $R^4$, $R^5$ and $R^6$ are independently (1) a hydrogen atom, (2) a halogen atom, (3) a cyano group, (4) a nitro group, (5) a $C_{1-4}$ acyl group, (6) a $C_{1-4}$ alkoxy group which may be substituted with halogen, (7) a $C_{1-4}$ alkyl group which may be substituted with halogen or (8) a mercapto group which may be substituted with a $C_{1-4}$ alkyl group.

Examples of the halogen atom (2) include fluorine, chlorino, bromine, and iodine. Among others, fluorine, chlorine and bromine are preferred and fluorine and bromine are more preferred.

Examples of the $C_{1-4}$ acyl group (5) include $C_{1-4}$ acyl groups derived from carboxylic acid, sulfinic acid or sulfonic acid, preferably a $C_{1-4}$ acyl group derived from sulfonic acid.

Examples of the $C_{1-4}$ acyl group derived from carboxylic acid include a $C_{1-4}$ alkanoyl group (for example, formyl, acetyl, propionyl, butyryl, isobutyryl), and a $C_{3-4}$ cycloalkyl-carbonyl group (for example, cyclopropylcarbonyl), among others, a $C_{1-4}$ alkanoyl group is preferred.

Examples of the $C_{1-4}$ acyl group derived from sulfinic acid include a $C_{1-4}$ alkylsulfinyl group (for example, methylsulfinyl, ethylsulfinyl, propylsulfinyl, isopropylsulfinyl, butylsulfinyl, isobutylsulfinyl, t-butylsulfinyl), and a $C_{3-4}$ cycloalkylsulfinyl group (for example, cyclopropylsulfinyl), and among others, a $C_{1-4}$ alkylsulfinyl group is preferred.

Examples of the $C_{1-4}$ acyl group derived from sulfonic acid include a $C_{1-4}$ alkylsulfonyl group (for example, methylsulfonyl, ethylsulfonyl, propylsulfonyl, isopropylsulfonyl, butylsulfonyl, isobutylsulfonyl, t-butylsulfonyl), and a $C_{3-6}$ cycloalkylsulfonyl group (for example, cyclopropylsulfonyl), and among others, a $C_{1-4}$ alkylsulfonyl group is preferred.

Such $C_{1-4}$ acyl groups may be substituted with 1 to 5 halogen atoms at replaceable positions (for example, $CF_3CO$, $CF_3SO_2$).

Preferable examples of the $C_{1-4}$ alkoxy group (for example, methoxy, ethoxy, propoxy, isopropoxy, butoxy, isobutoxy, t-butoxy) which may be substituted with halogen atom (for example, fluorine, chlorine, bromine, iodine) (6) include halogeno-$C_{1-4}$ alkoxy groups (for example, $C_{1-4}$ alkoxy groups substituted by 1 to 5 halogen atoms such as $CF_3O$ and $HCF_2O$).

Preferable examples of the $C_{1-4}$ alkyl group (for example, methyl, ethyl, propyl, isopropyl, butyl, isobutyl, t-butyl) which may be substituted with halogen atom (for example, fluorine, chlorine, bromine, iodine) (7) include halogeno-$C_{1-4}$ alkyl groups (for example, $C_{1-4}$ alkyl groups substituted by 1 to 5 halogen atoms such as $CF_3$, $CF_3CF_2$, $CH_2F$ and $CHF_2$, preferably $CF_3$).

Preferable examples of the mercapto group which may be substituted with $C_{1-4}$ alkyl group (for example, methyl, ethyl, propyl, isopropyl, butyl, isobutyl, t-butyl) (8) include $C_{1-4}$ alkylthio groups (for example, methylthio, ethylthio).

Preferable examples of $R^4$, $R^5$ and $R^6$ are independently (1) a hydrogen atom, (2) a halogen atom, (3) a cyano group, (4) a nitro group or (7) a $C_{1-4}$ alkyl group which may be substituted with halogen. Among others, (1) a hydrogen atom and (2) a halogen atom are preferred and more preferably, $R^4$ and $R^5$ are a halogen atom and $R^6$ is a hydrogen atom. The most preferable example is a combination in which $R^4$ is bromine, $R^5$ is fluorine and $R^6$ is a hydrogen atom.

The compound [I] of this invention has geometrical isomers, in the structure portion of oxime or imine, based on the steric configuration of pyridyl group and Q group, and it can exist as an E- or Z-isomer or a mixture of them. The present invention includes each of the isomers and a mixture of them. Preferable are a Z-isomer and a mixture of E and Z, and more preferable is a Z-isomer.

Examples of salts of the compound [I] include pharmaceutically acceptable salts such as salts with inorganic acids or organic acids, alkali metal salts, alkaline metal salts, and salts with bases such as ammonium or a substituted ammonium.

Preferred practical examples of the compound [I] include
(Z)-2-[3-bromo-α-(t-butoxyimino)benzyl]-3-hydroxypyridine or a salt thereof,
(Z)-2-[3-bromo-α-(t-butoxyimino)benzyl]-3-hydroxypyridine N-oxide or a salt thereof,
(Z)-2-[α-(t-butoxyimino)-4-chlorobenzyl]-3-hydroxypyridine N-oxide or a salt thereof,
(Z)-2-[α-(t-butoxyimino)-3,4-dichlorobenzyl]-3-hydroxypyridine N-oxide or a salt thereof,
(Z)-2-[α-(t-butoxyimino)-3,5-dichlorobenzyl]-3-hydroxypyridine or a salt thereof,
(Z)-2-[3-bromo-α-(t-butoxyimino)-4-fluorobenzyl]-3-hydroxypyridine or a salt thereof,
(Z)-2-[α-(t-butoxyimino)-3-trifluoromethylbenzyl]-3-hydroxypyridine or a salt thereof,
(Z)-2-[α-(t-butoxyimino)-3-nitrobenzyl]-3-hydroxypyridine or a salt thereof,
(Z)-2-[3-bromo-α-(t-butoxyimino)-4-fluorobenzyl]-3-hydroxypyridine N-oxide or a salt thereof, and
(Z)-2-[3-bromo-α-(t-butylhydrazono)benzyl]-3-hydroxypyridine N-oxide or a salt thereof.

More preferable examples of the compound [I] include
(Z)-2-[3-bromo-α-(t-butoxyimino)benzyl]-3-hydroxypyridine or a salt thereof,
(Z)-2-[α-(t-butoxyimino)-3,5-dichlorobenzyl]-3-hydroxypyridine or a salt thereof,
(Z)-2-[3-bromo-α-(t-butoxyimino)-4-fluorobenzyl]-3-hydroxypyridine or a salt thereof,
(Z)-2-[α-(t-butoxyimino)-3-trifluoromethylbenzyl]-3-hydroxypyridine or a salt thereof,
(Z)-2-[α-(t-butoxyimino)-3-nitrobenzyl]-3-hydroxypyridine or a salt thereof, and
(Z)-2-[3-bromo-α-(t-butoxyimino)-4-fluorobenzyl]-3-hydroxypyridine N-oxide or a salt thereof.

In this specification, the desired compound [I] or a salt thereof or starting or intermediate compounds therefor or a salt thereof may occasionally be abbreviated only as the desired compound [I] or the starting or intermediate compounds with the omission of "a salt thereof".

The compound [I] of this invention can be produced by, for example, allowing a compound of the formula [II]:

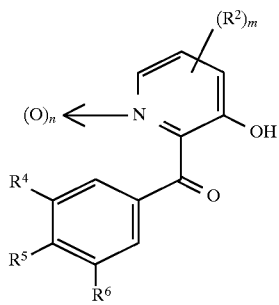

wherein symbols are of the same meaning as defined above, or a salt thereof to react with a compound of the formula [III]:

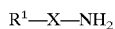

wherein the symbol is of the same meaning as defined above or a salt thereof. The compound [III] or a salt thereof is employed usually in an amount ranging from about 1 to 2 moles relative to one mole of the compound [II] or a salt thereof. This reaction can be allowed to proceed smoothly by, upon necessity, adding triethylamine, pyrrolidine, sodium acetate, boron trifluoride-diethylether, etc. as the catalyst in an amount ranging from 1/10 to 3 times as much moles.

For example, this condensation reaction can be conducted in an inert solvent such as methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF), dimethylsulfoxide (DMSO), acetic acid, pyridine or water, or a mixed solvent of them. The reaction is conducted at a temperature ranging from about −50° C. to 180° C.

Further, one or more groups of $R^4$, $R^5$ and/or $R^6$ in the compound [I] can be converted into different groups of $R^4$, $R^5$ and/or $R^6$. For example, following per se known methods, a hydrogen atom can be substituted with a halogen atom by halogenation or a nitro group by nitration. A cyano group can also be converted into a formyl group by using Raney's nickel in water/acetic acid/pyridine in the presence of sodium phosphate.

And, the pyridyl group can be converted into a pyridine-N-oxide group by oxidation with m-chloroperbenzoic acid, perbenzoic acid, p-nitroperbenzoic acid, pentafluoroperbenzoic acid, monoperphthalic acid, magnesium monoperoxyphthalate, peracetic acid, hydrogen peroxide or the like.

Desirably, the conditions of this oxidation reaction may be appropriately changed depending upon an oxidant then employed. For example, when m-chloroperbenzoic acid is employed, the reaction is carried out in an inert solvent such as dichloromethane, chloroform, 1,2-dichloroethane, diethylether, tetrahydrofuran, acetone, ethyl acetate or the like, or a mixed solvent thereof. The oxidant is employed in an amount ranging from about 1 to 2 moles relative to one mole of the pyridine derivative. The reaction is carried out at a temperature usually ranging from −25° C. to 80° C., preferably ranging from −25° to 25° C.

The compound [II] to be employed as the starting material can be produced by known methods or similar methods, or can be produced by, for example, methods as shown in the Reaction Scheme I and methods disclosed by the following reference examples.

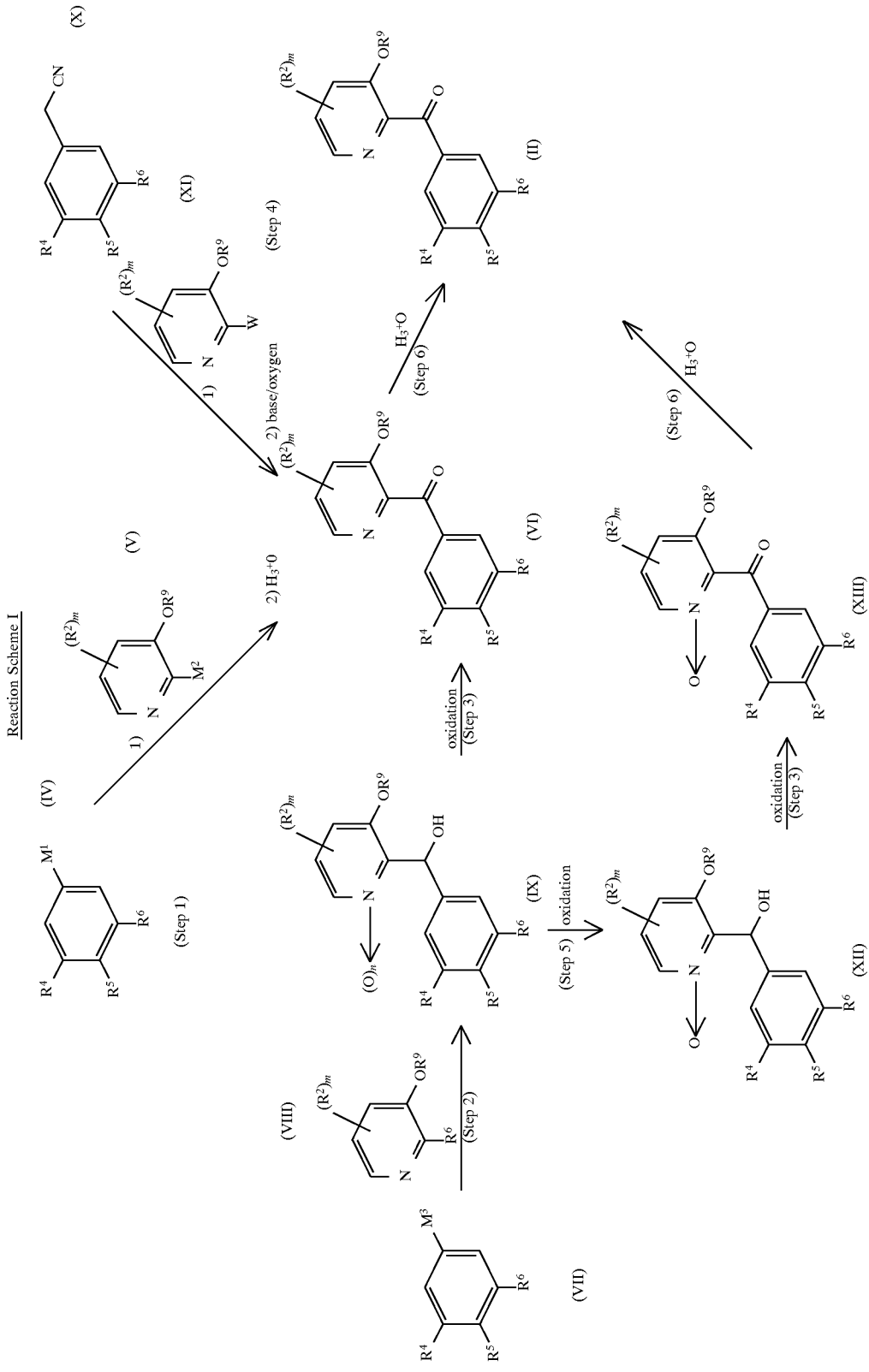
Reaction Scheme I

More specially, the compound [II] can be produced by allowing a compound of the formula [IV]:

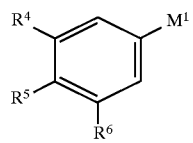

to react with a compound of the formula [V]:

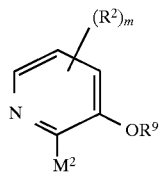

wherein one of $M^1$ and $M^2$ is CN and the other stands for a leaving group; $R^9$ is a hydroxyl-protecting group; other symbols are of the same meaning as defined above, then by subjecting the reaction product to acid-hydrolysis to give a ketone compound of the formula [VI]:

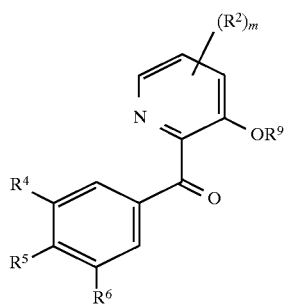

wherein symbols are of the same meaning as defined above, followed by subjecting the compound [VI] to deprotection.

The ketone compound of the formula [VI] can also be produced by, for example, allowing a compound of the formula [VII]:

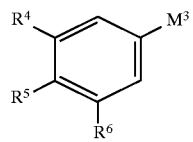

to react with a compound of the formula [VIII]:

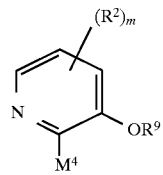

wherein one of $M^3$ and $M^4$ is CHO and the other is a leaving group, and other symbols are of the same meaning as defined above, to give an alchohol compound of the formula [IX]:

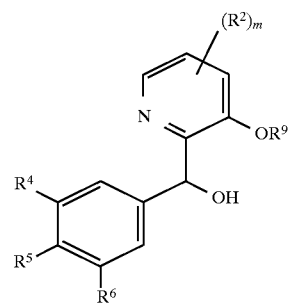

wherein symbols are of the same meaning as defined above, followed by subjecting the compound [IX] to oxidation.

And, the compound of the formula [VI] can also be produced by allowing a compound of the formula [X]:

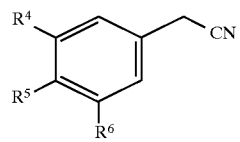

wherein all symbols are of the same meaning as defined above, to react with a compound of the formula [XI]:

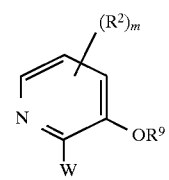

wherein W is a halogen atom; and other symbols are of the same meaning as defined above, in the presence of a basic catalyst, followed by subjecting the reaction product to oxidative decyanation.

Further, the compound [II] wherein n is 1 can also be produced by allowing the compound of the formula [IX] to oxidation to give a N-oxide compound of the formula [XII]:

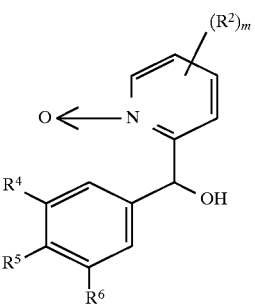

wherein symbols are of the same meaning as defined above, then by subjecting the compound [XII] to oxidation to give a ketone compound of the formula [XIII]:

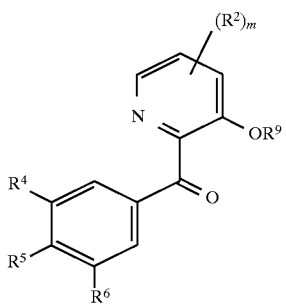

[XIII]

followed by subjecting the compound [XIII] to deprotection.

In the above formulae, preferable examples of leaving groups represented by $M^1$ to $M^4$ include alkali metals, alkaline earth metals or their halogenides (for example, Li, Na, K, Ca (1/2), $MgCl_2$, $MgBr_2$, $MgI_2$), zinc compounds (for example, $ZnCl_2$) and tin compounds (for example, $SnCl_2$).

Preferable examples of the hydroxyl-protecting groups shown by $R^9$ in the formulae [V], [VI], [VIII], [IX], [XI], [XII] and [XIII] include per se known protecting groups of phenolic hydroxyl groups, such as methoxydimethylmethyl group, trimethylsilyl group, t-butyldimethylsilyl group, trimethylsilylethoxymethyl (SEM) group, methoxymethyl group, benzyloxymethyl group and tetrahydropyranyl (THP) group.

Each step is illustrated below in detail.

(Step 1)

This condensation reaction is carried out in an inert solvent such as tetrahydrofuran, diethyl ether, dimethoxyethane, hexane, toluene, benzene or methylene chloride or a mixed solvent thereof at a temperature ranging from about −80° C. to 70° C. This reaction is conducted preferably under atmosphere of an inert gas (for example, nitrogen or argon).

Imine compounds then produced are converted into ketone compounds by a per se known method, for example, hydrolysis or alcoholysis.

(Step 2)

This condensation reaction is also conducted in substantially the same manner as in Step 1.

(Step 3)

Oxidation reaction of the benzyl alcohol compound then produced is conducted by a per se known method, for example, by using an about 2 to 10 times as much weight of activated manganese dioxide as an oxidizing agent in an inert solvent such as benzene, toluene, chloroform, dichloromethane, 1,2-dichloroethane, tetrahydrofuran, diethyl ether or hexane, or a mixed solvent thereof, at a temperature ranging from about 0° C. to 100° C.

(Step 4)

The condensation reaction of the benzyl cyanide compound [X] with the halogenopyridine compound [XI] is carried out in an inert solvent such as benzene, toluene, chloroform, dichloromethane, 1,2-dichloroethane, diethyl ether, tetrahydrofuran or DMF or a mixed solvent thereof in the presence of a base at a temperature ranging from about 0° C. to 100° C. As the base, mention is made of lithium hydride, sodium hydride, sodium methoxide, sodium ethoxide, potassium t-butoxide or the like. This reaction can be allowed to proceed smoothly by, upon necessity, adding about 1 to 3 times as much moles of sodium benzenesulfinate, sodium p-toluenesulfinate or the like. This reaction is carried out, preferably, under atmosphere of an inert gas (for example, nitrogen, argon or the like).

The oxidative decyanation to be followed is carried out, preferably, for example, in an inert organic solvent (for example, dichloromethane, 1,2-dichloroethane, chloroform, benzene, toluene, DMF and DMSO), or a mixed solvent (a hydrated solvent) thereof, in the presence of a base (sodium hydroxide, potassium hydroxide, sodium carbonate, potassium carbonate or the like), by, upon necessity, adding a phase-transfer catalyst (tetrabutyl ammonium hydrogensulfate, benzyl a triethyl ammonium chloride or the like), at a temperature ranging from about 10° C. to 50° C.

(Step 5)

As the oxidizing agent to be employed in this reaction, mention is made of, for example, m-chloroperbonzoic acid, perbenzoic acid, p-nitroperbenzoic acid, pentafluoroperbenzoic acid, permonophthalic acid, magnesium monoperoxyphthalate, peracetic acid and hydrogen peroxide.

The conditions of this reaction may be desirably changed depending on the oxidizing agent then employed. For example, in the case where m-chloroperbenzoic acid is employed, the reaction is carried out in an inert solvent such as dichloromethane, chloroform, 1,2-dichloroethane, diethyl ether, tetrahydrofuran, acetone, ethyl acetate or the like, or a mixed solvent thereof at a temperature ranging from −25° C. to 80° C.

(Step 6)

Provided that, in all the production methods mentioned above, when the benzene ring has a an acyl group derived from carboxylic acid as the substituent, the carbonyl moiety is protected with, for example, 1,3-dioxolan-2-yl by a per se conventional method, which is then subjected to acid-hydrolysis, followed by deprotection to thereby revert to an acyl group derived from carboxylic acid.

Among the above-mentioned desired compounds or starting compounds, intermediate compounds can be converted into salts thereof by using an acid, in accordance with a conventional procedure. Suitable acids for this reaction are preferably those which can give pharmaceutically acceptable salts. They include inorganic acids such as hydrochloric acid, hydrobromic acid, phosphoric acid, sulfuric acid, nitric acid and sulfamic acid, and organic acids such as acetic acid, tartaric acid, citric acid, fumaric acid, maleic acid, p-toluenesulfonic acid, methanesulfonic acid and glutamic acid. And, when the compound thus obtained is in a form of a salt, it may be converted into a free base in accordance with a conventional manner.

And, the above-mentioned desired compounds or starting or intermediate compounds therefor having acid groups such as —COOH, —$SO_2H$ and —$SO_3H$ can be converted into salts thereof, in accordance with conventional methods.

Preferable examples of salts include salts with bases such as alkali metals, alkaline earth metals, ammonium or a substituted ammonium, and more specially, salts with sodium, potassium, lithium, calcium, magnesium, aluminum, zinc, ammonium, tri-$C_{1-4}$ alkylammonium (for example, trimethylammonium, triethylammonium), triethanolammonium, etc.

In each reaction described above, unless otherwise mentioned, the starting materials are used in an equimolar amount, and the reaction time ranges usually from 1 to 24 hours.

The desired compound [I] or its intermediate compounds thus obtained can be isolated from a reaction mixture by conventional isolation and purification procedures, for example, extraction, concentration, neutralization, filtration, recrystallization and column (or thin-layer) chromatography.

The compounds [I] of this invention exhibits smooth muscle relaxation activity, coronary blood-flow increasing activity, antihypertensive activity, ischemic cardiomuscular protective activities and liponetabolic ameliorative activities in animals, especially mammals (for example, human, monkey, dog, cat, rabbit, guinea pig, rat and mouse), which is considered to be based on potassium channel opening (activating) activity, and they are useful as therapeutic and prophylactic agents against, for example, angina pectoris, myocardial infarction, congestive heart failure, hypertension, asthma, cerebrovascular contraction, arrhythmia, cerebral hemorrhage, dysmenorrhea, renal insufficiency, peripheral angiemphraxis, enuresis, gastrointestinal disorders (especially irritable intestinal syndrome), epilepsia, and alopecia. Preferably, they are useful as agent for treating or preventing cardiovascular disease such as angina pectoris and hypertension.

The compounds [I] of this invention are low in toxicity, well absorbed even through oral administration and high in stability. Therefore, when the compounds [I] are used as the medicines as described above, they can be safely administered orally or non-orally as they are, or in the form of a pharmaceutical composition prepared by admixing them with suitable pharmaceutically acceptable carriers, excipients or diluents, as exemplified by powders, granules, tablets, capsules (including soft capsules and microcapsules), liquids, injections, suppositories and the like. The dosage varies with subject patients, administration routes and conditions of diseases to be treated. In the case of oral administration to an adult human patient for the treatment of, for example, angina pectoris or hypertension, one dosage ranges usually from about 0.001 to 10 mg/kg, preferably from 0.001 to 0.2 mg/kg, more preferably from 0.001 to 0.02 mg/kg. It is desirable to administer the above dosage about one to three times a day depending on symptoms of the patients.

The following Reference Examples describing the production of the starting materials, Examples describing the desired compounds [I] of this invention and Experimental Examples describing pharmacological actions of the compounds [I] further illustrate the present invention in more detail, but they are not to be construed to limit the scope of this invention.

EXAMPLES

Reference Example 1

(Production of compound A-1)

To a solution of 2-bromo-3-methoxymethoxypyridine (9.11 g) in diethyl ether (200 mL) was added, at −78° C., a 1.6M n-butyl lithium hexane solution (29 mL). The mixture was stirred for one hour at the same temperature, to which was further added a solution of 3-bromobenzaldehyde (6.0 mL) in diethyl ether (5 mL), and the mixture was stirred for one hour at the same temperature. The reaction mixture was poured into water, which was subjected to extraction with ethyl acetate. The extract was washed with a saturated aqueous saline solution, which was then dried (sodium sulfate) and concentrated. The concentrate was purified by means of a silica gel column (ethyl acetate—hexane) to afford 2-(3-bromo-α-hydroxybenzyl)-3-methoxymethoxypyridine (10.89 g) (compound A-1). Physical properties and spectrum data of the product are shown in Table 1 and Table 2. In substantially the same manner as above, compounds A-2 to A-4, and A-6 to A-7 shown in Table 1 were produced.

Reference Example 2

(Production of compound A-5)

To a solution of 2-bromo-3-methoxymethoxypyridine (11.8 g) in diethyl ether (250 mL) was added, at −78° C., a 1.6M n-butyl lithium hexane solution (36.0 mL). The mixture was stirred for one hour at the same temperature, to which was further added a solution of 3-bromo-4-fluorobenzaldehyde (10.0 g) in diethyl ether (50 mL), and the mixture was stirred for one hour at the same temperature. The reaction mixture was poured into water, which was subjected to extraction with ethyl acetate. The extract was washed with a saturated aqueous saline solution, which was then dried (sodium sulfate) and concentrated. The concentrate was purified by means of a silica gel column (ethyl acetate—hexane) to afford 2-(3-bromo-4-fluoro-α-hydroxybenzyl)-3-methoxymethoxypyridine (14.0 g) (compound A-5). Physical properties and spectrum data of the product are shown in Table 1 and Table 2.

Reference Example 3

(Production of compound B-1)

A mixture of 2-(3-bromo-α-hydroxybenzyl)-3-methoxymethoxypyridine (6.43 g), activated manganese dioxide (18.4 g) and ethyl acetate (50 mL) was stirred overnight at room temperature, which was then subjected to filtration. The filtrate was subjected to concentration under reduced pressure. The concentrate was purified by means of a silica gel column (ethyl acetate—hexane) to afford 2-(3-bromobenzoyl)-3-methoxymethoxypyridine (5.55 g) (compound B-1). Physical properties and spectrum data of the product are shown in Table 3 and Table 4. In substantially the same manner as above, compounds B-2 to B-4, B-7 and B-8 shown in Table 3 were produced.

Reference Example 4

(Production of compound B-5)

A mixture of 2-(3-bromo-4-fluoro-α-hydroxy-benzyl)-3-methoxymethoxypyridine (14.0 g), activated manganese dioxide (41.8 g) and ethyl acetate (200 mL) was stirred overnight at room temperature, which was then subjected to filtration. The filtrate was concentrated under reduced pressure. The concentrate was purified by means of a silica gel column (ethyl acetate—hexane) to afford 2-(3-bromo-4-fluorobenzoyl)-3-methoxymethoxypyridine (13.0 g) (compound B-5). Physical properties and spectrum data of the product are shown in Table 3 and Table 4.

Reference Example 5

(Production of compound B-6)

To a solution of 2-(3-bromo-4-fluorobenzoyl)-3-methoxymethoxypyridine (4.68 g) in dimethyl sulfoxide (50 mL) was added potassium cyanide (2.7 g) at 0° C. The mixture was stirred for 3 hours while raising the temperature to room temperature. The reaction mixture was poured into water, which was subjected to extraction with ethyl acetate. The extract solution was washed with water and a saturated aqueous saline solution, successively, and dried (sodium sulfate) and then concentrated. The concentrate was purified by means of a silica gel column (ethyl acetate—hexane) to afford 2-(3-bromo-4-cyanobenzoyl)-3-methoxymethoxypyridine (4.59 g) (compound B-6). Physical properties and spectrum date of the product are shown in Table 3 and Table 4.

Reference Example 6

(Production of compound C-1)

A mixture of 2-(3-bromobenzoyl)-3-methoxymethoxy pyridine (5.55 g), 3.6N-sulfuric acid (11 mL) and acetone (30 mL) was subjected to reflux for 3 hours. The reaction mixture was poured into water, neutralized with an aqueous solution of sodium hydroxide, and extracted with ethyl acetate. The extract was washed with water and a saturated aqueous saline solution, successively, and dried (sodium sulfate) and then concentrated. The concentrate was purified by means of a silica gel column (ethyl acetate—hexane) to afford 2-(3-bromobenzoyl)-3-hydroxypyridine (4.46 g) (compound C-1). Physical properties and spectrum date of the product are shown in Table 5 and Table 6. In substantially the same manner as above, compounds C-2 to C-4 and C-6 to C-9 shown in Table 5 were produced.

Reference Example 7

(Production of compound C-5)

A mixture of 2-(3-bromo-4-fluorobenzoyl)-3-methoxymethoxypyridine (5.68 g), 3.6N-sulfuric acid (6.0 mL) and acetone (30 mL) was refluxed for 3 hours. The reaction mixture was then poured into water, neutralized with a saturated aqueous solution of sodium hydroxide, and extracted with ethyl acetate. The extract was washed with water and a saturated aqueous saline solution, successively, and dried (sodium sulfate) and then concentrated. The concentrate was purified by means of a silica gel column (ethyl acetate—hexane) to afford 2-(3-bromo-4-fluorobenzoyl)-3-hydroxypyridine (4.51 g) (compound C-5). Physical properties and spectrum date of the product are shown in Table 5 and Table 6.

Reference Example 8

A mixture of 2-(3-bromo-α-hydroxybenzyl)-3-methoxymethoxy pyridine (4.65 g), 70% m-chloroperbenzoic acid (7.10 g) and tetrahydrofuran (200 mL) was stirred overnight at room temperature, to which was poured an aqueous solution of sodium sulfite. The mixture was stirred for 30 minutes, and then subjected to extraction with ethyl acetate. The extract was washed with water and a saturated aqueous saline solution, successively, and dried (sodium sulfate) and then concentrated. The concentrate was purified by means of a silica gel column (ethyl acetate—hexane) to afford 2-(3-bromo-α-hydroxybenzyl)-3-methoxymethoxypyridine 1-oxide (4.58 g). Spectrum data of the product are shown below:

$^1$H-NMR(CDCl$_3$): δ 3.53(3H,s), 5.33(2H,s), 6.32(1H,d, J=9.6 Hz), 7.15–7.62(6H,m), 7.90(1H,d,J=6.2 Hz)

Reference Example 9

A suspension of 2-(3-bromo-α-hydroxybenzyl)-3-methoxymethoxypyridine 1-oxide (4.58 g) and activated manganese dioxide (13.1 g) in ethyl acetate (150 mL) was stirred overnight at room temperature. The reaction mixture was subjected to filtration, and the filtrate was concentrated under reduced pressure. The concentrate was purified by means of a silica gel column (ethyl acetate—hexane) to afford 2-(3-bromobenzoyl)-3-methoxymethoxy pyridine 1-oxide (4.29 g). Physical properties and spectrum data of the product are shown below:

Melting point 126°–127° C.

$^1$H-NMR(CDCl$_3$): δ 3.38(3H,s), 5.17(2H,s), 7.21–7.41 (3H,m), 7.71–7.79(2H,m), 7.96–8.00(2H,m)

Reference Example 10

A mixture of 2-(3-bromobenzoyl)-3-methoxymethoxy pyridine 1-oxide (4.00 g), 3.6N-sulfuric acid (11 mL) and acetone (50 mL) was refluxed for 5 hours. The reaction mixture was poured into water, neutralized with an aqueous solution of sodium hydroxide, and extracted with ethyl acetate. The extract was washed with water and a saturated aqueous saline solution, successively, and dried (sodium sulfate) and then concentrated. The concentrate was purified by means of a silica gel column (ethyl acetate—hexane) to afford 2-(3-bromobenzoyl)-3-hydroxypyridine 1-oxide (2.81 g). Physical properties and spectrum data of the product are shown below.

Melting point 200°–202° C.

$^1$H-NMR(CDCl$_3$): δ 7.04(1H,d,J=8.8 Hz), 7.36–7.56(2H, m), 7.69–7.73(1H,m), 7.83–7.91(3H,m), 11.12(1H,s)

Example 1

(Production of compounds 1 and 2)

A mixture of 2-(3-bromobenzoyl)-3-hydroxypyridine (1.78 g), O-t-butylhydroxylamine hydrochloride (1.19 g) and ethanol (50 mL) was refluxed for 5 hours. The reaction mixture was poured into water, and subjected to extraction with ethyl acetate. The extract was washed with water and a saturated aqueous saline solution, successively, and dried (sodium sulfate), followed by evaporating the solvent under reduced pressure. The residue was purified by means of a silica gel column (ethyl acetate—hexane) to afford (E)-2-(3-bromo-α-t-butoxyiminobenzyl)-3-hydroxypyridine (0.83 g) and (Z)-2-(3-bromo-α-t-butoxyiminobenzyl)-3-hydroxypyridine (0.83 g) and (Z)-2-(3-bromo-α-t-butoxyiminobenzyl)-3-hydroxypyridine (1.12 g) (compounds 2 and 1). In substantially the same manner as above, compounds 5, 6, 10, 13, 14, 18 to 24 were produced. Physical properties and spectrum data of these compounds and those produced in the following Examples are shown in Table 7 to Table 11.

Example 2

(Production of compound 3)

A mixture of (Z)-2-(3-bromo-α-t-butoxyiminobenzyl)-3-hydroxypyridine (0.49 g), 70% m-chloroperbenzoic acid (0.70 g) and tetrahydrofuran (30 mL) was stirred overnight at room temperature. To the reaction mixture was added an aqueous solution of sodium sulfite. The reaction mixture was stirred for 30 minutes, and extracted with ethyl acetate. The extract was washed with water and a saturated aqueous saline solution, successively, and dried (sodium sulfate) and then concentrated. The concentrate was crystallized from isopropyl ether, and recrystallized from ethanol-water to afford (Z)-2-(3-bromo-α-t-butoxyiminobenzyl)-3-hydroxypyridine 1-oxide (0.41 g) (compound 3). In substantially the same manner as above, compounds 4, 7, 8, 11, 12 and 15 were produced.

Example 3

(Production of compounds 16 and 17)

A mixture of 2-(3-bromo-4-fluorobenzoyl)-3-hydroxypyridine (1.26 g), O-t-butylhydroxylamine hydrochloride (1.08 g) and ethanol (10 mL) was refluxed for 2 hours. The reaction mixture was poured into water, and subjected to extraction with ethyl acetate. The extract was washed with water and a saturated aqueous saline solution, successively, and dried (sodium sulfate), followed by evaporating the solvent under reduced pressure. The residue was subjected to purification by means of a silica gel column (ethyl acetate—hexane) to afford (E)-2-(3-bromo-α-t-butoxyimino-4-fluorobenzyl)-3-hydroxypyridine (0.89 g) and (Z)-2-(3-bromo-α-t-butoxyimino-4-fluorobenzyl)-3-hydroxypyridine (0.51 g) (compounds 17 and 16).

Example 4

(Production of compound 25)

A mixture of (Z)-2-(3-bromo-α-t-butoxyimino-4-fluorobenzyl)-3-hydroxypyridine (0.55 g), 70% m-chloro perbenzoic acid (0.74 g) and tetrahydrofuran (10 mL) was stirred overnight at room temperature. To the reaction mixture was added an aqueous solution of sodium sulfite. The reaction mixture was stirred for 30 minutes, and subjecting to extraction with ethyl acetate. The extract was washed with water and a saturated aqueous saline solution, successively, and dried (sodium sulfate) and then concentrated. The concentrate was crystallized from isopropyl ether, and recrystallized from ethanol-water to afford (Z)-2-(3-bromo-α-t-butoxyimino-4-fluorobenzyl)-3-hydroxypyridine 1-oxide (0.46 g) (compound 25).

Example 5

(Production of compounds 26 and 27)

A mixture of 2-(3-bromobenzoyl)-3-hydroxypyridine (0.79 g), t-butylhydrazine hydrochloride (0.53 g), triethylamine (1.2 mL) and ethanol (13 mL) was refluxed for 5 hours. The reaction mixture was poured into water, and subjected to extraction with ethyl acetate. The extract was washed with water and a saturated aqueous saline solution, successively, and dried (sodium sulfate), followed by evaporating the solvent under reduced pressure. The residue was purified by means of a silica gel column (ethyl acetate—hexane) to afford (E)-2-(3-bromo-α-t-butylhydrazinobenzyl)-3-hydroxypyridine (0.60 g) and (Z)-2-(3-bromo-α-t-butylhydrazonobenzyl)-3-hydroxypyridine (0.24 g) (compounds 27 and 26).

Example 6

(Production of compounds 28 and 29)

A mixture of 2-(3-bromobenzoyl)-3-hydroxypyridine 1-oxide (2.13 g), t-butylhydrazine hydrochloride (3.03 g), triethylamine (3.5 mL) and ethanol (50 mL) was refluxed for 2 hours. The reaction mixture was then poured into a saturated aqueous saline solution, and subjected to extraction with ethyl acetate. The extract was washed with a saturated aqueous saline solution, and dried (sodium sulfate), followed by evaporating the solvent under reduced pressure. The residue was purified by means of a silica gel column (ethyl acetate—hexane) to afford (E)-2-(3-bromo-t-butylhydrazonobenzyl)-3-hydroxypyridine 1-oxide (0.68 g) and (Z)-2-(3-bromo-α-t-butylhydrazonobenzyl)-3-hydroxypyridine 1-oxide (0.79 g) (compounds 29 and 28).

Example 7

(Production of compounds 16 and 17)

A mixture of 2-(3-bromo-4-fluorobenzoyl)-3-hydroxypyridine (2.96 g), O-t-butyl hydroxylamine hydrochloride (1.88 g) and acetic acid (50 mL) was stirred at 90° C. for 14 hours. The reaction mixture was concentrated in vacuo, which was subjected to addition with ethyl acetate and water. The ethyl acetate solution was washed with aqueous $NaHCO_3$ and a saturated aqueous saline solution, successively, which was dried (magnesium sulfate), followed by distilling off the solvent under reduced pressure. The residue was subjected to purification by means of a silica gel column (ethyl acetate—hexane) to afford (E)-2-(3-bromo-α-t-butoxyimino-4-fluorobenzyl)-3-hydroxypyridine (1.10 g) and (Z)-2-(3-bromo-α-t-butoxyimino-4-fluorobenzyl)-3-hydroxypyridine (1.97 g) (compounds 17 and 16).

TABLE 1

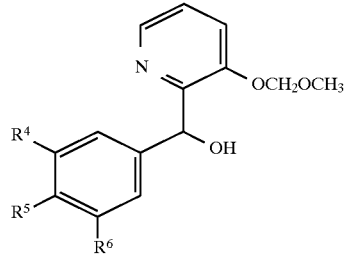

| Cpd. No. | $R^4$ | $R^5$ | $R^6$ | Formula | m.p. (°C.) |
|---|---|---|---|---|---|
| A-1 | Br | H | H | $C_{14}H_{14}NO_3Br$ | oil |
| A-2 | H | Cl | H | $C_{14}H_{14}NO_3Cl$ | 44–45 |
| A-3 | Cl | Cl | H | $C_{14}H_{13}NO_3Cl_2$ | oil |
| A-4 | Cl | H | Cl | $C_{14}H_{13}NO_3Cl_2$ | oil |
| A-5 | Br | F | H | $C_{14}H_{13}NO_3BrF$ | oil |
| A-6 | $CF_3$ | H | H | $C_{14}H_{13}NO_3F_3$ | oil |
| A-7 | $NO_2$ | H | H | $C_{14}H_{14}N_2O_5$ | oil |

TABLE 2

| Cpd. No. | $^1$H-NMR(CDCl$_3$; TMS internal standard, ppm) |
|---|---|
| A-1 | 3.24(3H, s), 5.08(1H, d, J=7.0Hz), 5.21(1H, d, J=7.0Hz), 5.60–5.65(1H, m), 5.87–5.90(1H, m), 7.11–7.55(6H, m), 8.24(1H, dd, J=1.0&4.8Hz). |
| A-2 | 3.24(3H, s), 5.06(1H, d, J=7.0Hz), 5.16(1H, d, J=7.0Hz), 5.59(1H, s), 5.91(1H, s), 7.17–7.40(6H, m), 8.24(1H, dd, J=1.4&4.8Hz). |
| A-3 | 3.29(3H, s), 5.11(1H, d, J=7.0Hz), 5.21(1H, d, J=7.0Hz), 5.60(1H, d, J=6.6Hz), 5.89(1H, d, J=6.6Hz), 7.18–7.52(5H, m), 8.22–8.27(1H, m). |
| A-4 | 3.30(3H, s), 5.13(1H, d, J=7.0Hz), 5.24(1H, d, J=7.0Hz), 5.62(1H, d, J=6.6Hz), 5.87(1H, d, J=6.6Hz), 7.16–7.43(5H, m), 8.24(1H, dd, J=1.0&4.8Hz). |
| A-5 | 3.27(3H, s), 5.10(1H, d, J=7.0Hz), 5.21(1H, d, J=7.0Hz), 5.62(1H, d, J=6.6Hz), 5.88(1H, d, J=6.6Hz), 6.98–7.07(1H, m), 7.19–7.42(3H, m), 7.56–7.61(1H, m), 8.24(1H, dd, J=1.0&4.4Hz). |
| A-6 | 3.19(3H, s), 5.07(1H, d, J=7.0Hz), 5.21(1H, d, J=7.0Hz), 5.72(1H, d, J=6.8Hz), 5.99(1H, d, J=6.8Hz), 7.19–7.26(1H, m), 7.36–7.70(5H, m), 8.24–8.27(1H, m). |

TABLE 2-continued

| Cpd. No. | $^1$H-NMR(CDCl$_3$; TMS internal standard, ppm) |
|---|---|
| A-7 | 3.27(3H, s), 5.14(1H, d, J=7.0Hz), 5.23(1H, d, J=7.0Hz), 5.75(1H, d, J=6.4Hz), 6.04(1H, d, J=6.4Hz), 7.21–7.27(1H, m), 7.41–7.50(2H, m), 7.76–7.80(1H, m), 8.07–8.11(1H, m), 8.25–8.31(2H, m). |

TABLE 3

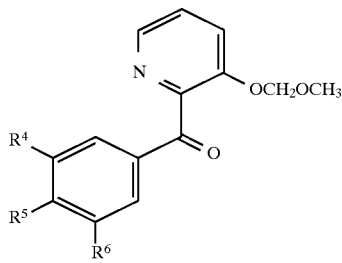

| Cpd. No. | R$^4$ | R$^5$ | R$^6$ | Formula | m.p. (°C.) |
|---|---|---|---|---|---|
| B-1 | Br | H | H | C$_{14}$H$_{12}$NO$_3$Br | oil |
| B-2 | H | Cl | H | C$_{14}$H$_{12}$NO$_3$Cl | oil |
| B-3 | Cl | Cl | H | C$_{14}$H$_{11}$NO$_3$Cl$_2$ | oil |
| B-4 | Cl | H | Cl | C$_{14}$H$_{11}$NO$_3$Cl$_2$ | oil |
| B-5 | Br | F | H | C$_{14}$H$_{11}$NO$_3$BrF | 57–58 |
| B-6 | Br | CN | H | C$_{15}$H$_{11}$N$_2$O$_3$Br | 107–108 |
| B-7 | CF$_3$ | H | H | C$_{15}$H$_{12}$NO$_3$F$_3$ | oil |
| B-8 | NO$_2$ | H | H | C$_{14}$H$_{12}$N$_2$O$_5$ | 110–111 |

TABLE 5-continued

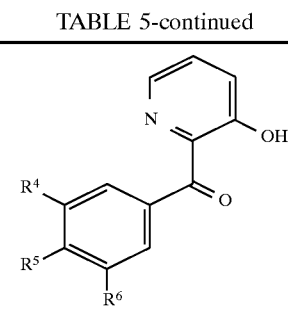

| Cpd. No. | R$^4$ | R$^5$ | R$^6$ | Formula | m.p. (°C.) |
|---|---|---|---|---|---|
| C-2 | H | Cl | H | C$_{12}$H$_8$NO$_2$Cl | 88–90 |
| C-3 | Cl | Cl | H | C$_{12}$H$_7$NO$_2$Cl$_2$ | 125–126 |
| C-4 | Cl | H | Cl | C$_{12}$H$_7$NO$_2$Cl$_2$ | 164–165 |
| C-5 | Br | F | H | C$_{12}$H$_7$NO$_2$BrF | 108–109 |
| C-6 | Br | CN | H | C$_{13}$H$_7$N$_2$O$_2$Br | 190 (dec.) |
| C-7 | CN | H | H | C$_{13}$H$_8$N$_2$O$_2$ | 126–128 |
| C-8 | CF$_3$ | H | H | C$_{13}$H$_8$NO$_2$F$_3$ | oil |
| C-9 | NO$_2$ | H | H | C$_{12}$H$_8$N$_2$O$_4$ | 116–117 |

TABLE 4

| Cpd. No. | $^1$H-NMR(CDCl$_3$; TMS internal standard, ppm) |
|---|---|
| B-1 | 3.42(3H, s), 5.18(2H, s), 7.24–7.82(5H, m), 7.99–8.01(1H, m), 8.33–8.36(1H, m). |
| B-2 | 3.41(3H, s), 5.18(2H, s), 7.36–7.45(3H, m), 7.60–7.65(1H, m), 7.80–7.85(2H, m), 8.33–8.35(1H, m). |
| B-3 | 3.43(3H, s), 5.19(2H, s), 7.42(1H, dd, J=4.4&8.4Hz), 7.54(1H, d, J=8.4Hz), 7.64(1H, dd, J=1.0&8.4Hz), 7.73(1H, dd, J=1.8&8.4Hz), 7.96(1H, d, J=1.8Hz), 8.35(1H, dd, J=1.0&4.4Hz). |
| B-4 | 3.44(3H, s), 5.20(2H, s), 7.43(1H, dd, J=4.6&8.6Hz), 7.57(1H, t, J=2.0Hz), 7.66(1H, dd, J=1.2&8.6Hz), 7.75(2H, d, J=2.0Hz), 8.36(1H, dd, J=1.2&4.6Hz). |
| B-5 | 3.43(3H, s), 5.20(2H, s), 7.16–7.24(1H, m), 7.42(1H, dd, J=4.4&8.4Hz), 7.64(1H, dd, J=1.2&8.4Hz), 7.81–7.89(1H, m), 8.10–8.14(1H, m), 8.35(1H, dd, J=1.2&4.4Hz). |
| B-6 | 3.45(3H, s), 5.22(2H, s), 7.46(1H, dd, J=4.6&8.8Hz), 7.69(1H, dd, J=1.2&8.8Hz), 7.76(1H, d, J=8.0Hz), 7.92(1H, dd, J=1.4&8.0Hz), 8.18(1H, d, J=1.4Hz), 8.36(1H, dd, J=1.2&4.6Hz). |
| B-7 | 3.42(3H, s), 5.20(2H, s), 7.43(1H, dd, J=4.8&8.4Hz), 7.57–7.69(2H, m), 7.82–7.86(1H, m), 8.05–8.15(2H, m), 8.36(1H, dd, J=1.2&4.8Hz). |
| B-8 | 3.45(3H, s), 5.23(2H, s), 7.47(1H, dd, J=4.6&8.6Hz), 7.65–7.73(2H, m), 8.27–8.48(3H, m), 8.68–8.70(1H, m). |

TABLE 5

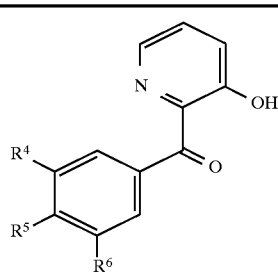

| Cpd. No. | R$^4$ | R$^5$ | R$^6$ | Formula | m.p. (°C.) |
|---|---|---|---|---|---|
| C-1 | Br | H | H | C$_{12}$H$_8$NO$_2$Br | 73–74 |

TABLE 6

| Cpd. No. | $^1$H-NMR(CDCl$_3$; internal standard, ppm) |
|---|---|
| C-1 | 7.35–7.47(3H, m), 7.71–7.76(1H, m), 8.12–8.18(1H, m), 8.31–8.36(2H, m), 11.96(1H, s). |
| C-2 | 7.44–7.50(4H, m), 8.18–8.31(3H, m), 12.05(1H, s). |
| C-3 | 7.42–7.52(2H, m), 7.58(1H, d, J=8.4Hz), 8.12(1H, dd, J=1.8&8.4Hz), 8.31(1H, dd, J=2.2&3.6Hz), 8.40(1H, d, J=1.8Hz), 11.92(1H, s). |
| C-4 | 7.42–7.52(2H, m), 7.58(1H, t, J=1.8Hz), 8.12(2H, d, J=1.8Hz), 8.32(1H, dd, J=2.2&3.2Hz), 11.79(1H, s). |
| C-5 | 7.20–7.29(1H, m), 7.45–7.47(2H, m), 8.25–8.33(2H, m), 8.57(1H, dd, J=2.2&7.0Hz), 11.96(1H, s). |
| C-6 | 7.45–7.55(2H, m), 7.80(1H, d, J=8.0Hz), 8.23(1H, dd, J=1.4&8.0Hz), 8.32(1H, dd, J=2.0&3.6Hz), 8.50(1H, d, J=1.4Hz), 11.70(1H, s). |
| C-7 | 7.44–7.54(2H, m), 7.61–7.69(1H, m), 7.85–7.91(1H, m), 8.31–8.34(1H, m), 8.41–8.46(1H, m), 8.62–8.64(1H, m), 11.87(1H, s). |
| C-8 | 7.43–7.52(2H, m), 7.60–7.68(1H, m), 7.84–7.88(1H, m), 8.30–8.33(1H, m), 8.40–8.50(2H, m), 11.94(1H, s). |
| C-9 | 7.49–7.51(2H, m), 7.67–7.75(1H, m), 8.32–8.58(3H, m), 9.13–9.15(1H, m), 11.85(1H, s). |

TABLE 7

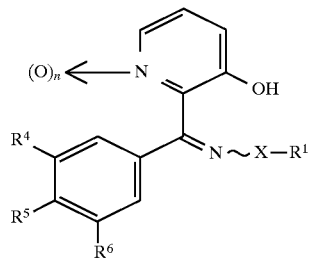

| Cpd. No. | R$^4$ | R$^5$ | R$^6$ | XR$^1$ | geometrical isomerism | n | Formula | m.p. (C.°) |
|---|---|---|---|---|---|---|---|---|
| 1 | Br | H | H | O$^t$Bu | Z | 0 | C$_{16}$H$_{17}$N$_2$O$_2$Br | 130–131 |
| 2 | Br | H | H | O$^t$Bu | E | 0 | C$_{16}$H$_{17}$N$_2$O$_2$Br | 84–85 |
| 3 | Br | H | H | O$^t$Bu | Z | 1 | C$_{16}$H$_{17}$N$_2$O$_3$Br | 253–254 |
| 4 | Br | H | H | O$^t$Bu | E | 1 | C$_{16}$H$_{17}$N$_2$O$_3$Br | 255–256 |
| 5 | H | Cl | H | O$^t$Bu | Z | 0 | C$_{16}$H$_{17}$N$_2$O$_2$Cl | 174–175 |
| 6 | H | Cl | H | O$^t$Bu | E | 0 | C$_{16}$H$_{17}$N$_2$O$_2$Cl | 104–105 |
| 7 | H | Cl | H | O$^t$Bu | Z | 1 | C$_{16}$H$_{17}$N$_2$O$_3$Cl | 191–193 |
| 8 | H | Cl | H | O$^t$Bu | E | 1 | C$_{16}$H$_{17}$N$_2$O$_3$Cl | 272 (dec.) |
| 9 | Cl | Cl | H | O$^t$Bu | Z | 0 | C$_{16}$H$_{16}$N$_2$O$_2$Cl$_2$ | 166–167 |
| 10 | Cl | Cl | H | O$^t$Bu | E | 0 | C$_{16}$H$_{16}$N$_2$O$_2$Cl$_2$ | 88–89 |
| 11 | Cl | Cl | H | O$^t$Bu | Z | 1 | C$_{16}$H$_{16}$N$_2$O$_3$Cl$_2$·1/2H$_2$O | 158–160 |
| 12 | Cl | Cl | H | O$^t$Bu | E | 1 | C$_{16}$H$_{16}$N$_2$O$_3$Cl$_2$·1/4H$_2$O | 268 (dec.) |
| 13 | Cl | H | Cl | O$^t$Bu | Z | 0 | C$_{16}$H$_{16}$N$_2$O$_2$Cl$_2$ | 203–204 |
| 14 | Cl | H | Cl | O$^t$Bu | E | 0 | C$_{16}$H$_{16}$N$_2$O$_2$Cl$_2$ | 100–101 |
| 15 | Cl | H | Cl | O$^t$Bu | Z | 1 | C$_{16}$H$_{16}$N$_2$O$_3$Cl$_2$·1/4H$_2$O | 236–238 |
| 16 | Br | F | H | O$^t$Bu | Z | 0 | C$_{16}$H$_{16}$N$_2$O$_2$BrF | 157–158 |
| 17 | Br | F | H | O$^t$Bu | E | 0 | C$_{16}$H$_{16}$N$_2$O$_2$BrF | 95–96 |
| 18 | Br | CN | H | O$^t$Bu | E | 0 | C$_{17}$H$_{16}$N$_3$O$_2$Br | 140–141 |
| 19 | CN | H | H | O$^t$Bu | Z | 0 | C$_{17}$H$_{17}$N$_3$O$_2$Cl$_2$·1/4H$_2$O | 185–186 |
| 20 | CN | H | H | O$^t$Bu | E | 0 | C$_{17}$H$_{17}$N$_3$O$_2$ | 121–122 |
| 21 | CF$_3$ | H | H | O$^t$Bu | Z | 0 | C$_{17}$H$_{17}$N$_2$O$_2$F$_3$ | 137–138 |
| 22 | CF$_3$ | H | H | O$^t$Bu | E | 0 | C$_{17}$H$_{17}$N$_2$O$_2$F$_3$ | 74–75 |
| 23 | NO$_2$ | H | H | O$^t$Bu | Z | 0 | C$_{17}$H$_{17}$N$_3$O$_4$ | 169–170 |
| 24 | NO$_2$ | H | H | O$^t$Bu | E | 0 | C$_{17}$H$_{17}$N$_3$O$_4$·1/5H$_2$O | 101–102 |
| 25 | Br | F | H | O$^t$Bu | Z | 1 | C$_{16}$H$_{16}$N$_2$O$_3$BrF | 218–219 |
| 26 | Br | H | H | NH$^t$Bu | Z | 0 | C$_{16}$H$_{18}$N$_3$OBr | 81–82 |
| 27 | Br | H | H | NH$^t$Bu | E | 0 | C$_{16}$H$_{18}$N$_3$OBr·1/2H$_2$O | 92–93 |
| 28 | Br | H | H | NH$^t$Bu | Z | 1 | C$_{16}$H$_{18}$N$_3$O$_2$Br | 183–185 |
| 29 | Br | H | H | NH$^t$Bu | E | 1 | C$_{16}$H$_{18}$N$_3$O$_2$Br | 179–180 |

TABLE 8

| Cpd. No. | ¹H-NMR(CDCl₃; TMS internal standard, ppm) | IR (KBr; cm⁻¹) |
|---|---|---|
| 1 | 1.47(9H, s), 7.15–7.64(7H, m), 8.29–8.33(1H, m). | 2980, 2610, 1575. |
| 2 | 1.37(9H, s), 7.17(1H, dd, J=4.4&8.2Hz), 7.28–7.38(3H, m), 7.52–7.58(2H, m), 8.13(1H, dd, J=1.4&4.4Hz), 11.29(1H, s). | 2970, 1580, 1560, 1430. |
| 3 | *1.26(9H, s), 6.90–6.97(1H, m), 7.26–7.39(3H, m), 7.52–7.61(2H, m), 7.82–7.88(1H, m), 10.70(1H, s). | 3050, 2975, 1560. |
| 4 | *1.30(9H, s), 6.97(1H, d, J=8.4Hz), 7.25–7.38(2H, m), 7.46–7.59(2H, m) 7.76–7.83(2H, m), 10.72(1H, s). | 3090, 2970, 1565. |
| 5 | 1.46(9H, s), 7.16(1H, s), 7.26–7.45(6H, m), 8.27–8.30(1H, m). | 2970, 2600, 1570. |
| 6 | 1.37(9H, s), 7.16(1H, dd, J=4.4&8.6Hz), 7.27–7.45(5H, m), 8.11(1H, dd, J=1.4&4.4Hz), 11.35(1H, s). | 3050, 2970, 1600, 1580. |
| 7 | *1.26(9H, s), 6.91(1H, d, J=8.4Hz), 7.28(1H, dd, J=6.6&8.4Hz), 7.36–7.46(4H, m), 7.83(1H, d, J=6.6Hz), 10.64(1H, s). | 3400, 2960, 1560. |

TABLE 9

| Cpd. No. | ¹H-NMR(CDCl₃; TMS internal standard, ppm) | IR (KBr; cm⁻¹) |
|---|---|---|
| 8 | *1.30(9H, s), 6.96(1H, d, J=8.6Hz), 7.28(1H, dd, J=6.4&8.6Hz), 7.41–7.47(2H, m), 7.54–7.60(2H, m), 7.80(1H, d, J=6.4Hz), 10.68(1H, s). | 2970, 2600, 1560. |
| 9 | 1.47(9H, s), 7.12(1H, s), 7.22(1H, dd, J=2.2&8.4Hz), 7.31–7.52(3H, m), 7.54(1H, d, J=2.2Hz), 8.29(1H, dd, J=1.6&4.0Hz). | 2970, 2600, 1570. |
| 10 | 1.37(9H, s), 7.14–7.25(2H, m), 7.34(1H, dd, J=1.6&8.6Hz), 7.48(1H, d, J=1.8Hz), 7.52(1H, d, J=8.4Hz), 8.12(1H, dd, J=1.6&4.4Hz), 11.18(1H, s). | 3060, 2970, 1575. |
| 11 | *1.27(9H, s), 6.94(1H, d, J=8.6Hz), 7.27–7.35(2H, m), 7.53(1H, d, J=1.8Hz), 7.63(1H, d, J=8.4Hz), 7.86(1H, d, J=6.2Hz), 10.73(1H, s). | 3400, 2975, 2500, 1565. |
| 12 | *1.30(9H, s), 6.98(1H, d, J=8.8Hz), 7.30(1H, dd, J=6.6&8.8Hz), 7.44(1H, dd, J=2.2&8.8Hz), 7.64(1H, d, J=8.8Hz), 7.79–7.83(2H, m), 10.78(1H, s). | 3090, 2970, 2620, 1565. |
| 13 | 1.47(9H, s), 7.07(1H, s), 7.23–7.47(5H, m), 8.31(1H, dd, J=1.4&4.4Hz). | 3050, 2975, 1565. |
| 14 | 1.38(9H, s), 7.15–7.42(5H, m), 8.13(1H, dd, J=1.4&4.4Hz), 11.09(1H, s). | 3050, 2960, 1575, 1560. |
| 15 | *1.27(9H, s), 6.95(1H, d, J=8.4Hz), 7.28–7.36(3H, m), 7.61–7.65(1H, m), 7.87(1H, d, J=6.2Hz), 10.77(1H, s). | 3050, 2970, 1560. |

TABLE 10

| Cpd. No. | ¹H-NMR(CDCl₃; TMS internal standard, ppm) | IR (KBr; cm⁻¹) |
|---|---|---|
| 16 | 1.46(9H, s), 7.04–7.16(2H, m), 7.26–7.46(3H, m), 7.64–7.69(1H, m), 8.29–8.32(1H, m). | 2980, 2775, 1570. |
| 17 | 1.38(9H, s), 7.15–7.24(2H, m), 7.30–7.38(2H, m), 7.60(1H, dd, J=2.0&6.6Hz), 8.13(1H, dd, J=1.4&4.4Hz), 11.24(1H, s). | 3050, 2975, 1575. |
| 18 | 1.37(9H, s), 7.20(1H, dd, J=4.4&8.4Hz), 7.36(1H, dd, J=1.4&8.4Hz), 7.42(1H, dd, J=1.4&8.0Hz), 7.68(1H, d, J=1.4Hz), 7.74(1H, d, J=8.0Hz), 8.10(1H, dd, J=1.4&4.4Hz), 10.94(1H, s). | 3040, 2960, 2220, 1580. |
| 19 | 1.48(9H, s), 7.15(1H, s), 7.34–7.49(3H, m), 7.64–7.69(2H, m), 7.75–7.78(1H, m), 8.28–8.31(1H, m). | 2980, 2600, 2220, 1570, 1445. |
| 20 | 1.37(9H, s), 7.19(1H, dd, J=4.4&8.4Hz), 7.36(1H, dd, J=1.6&8.4Hz), 7.52–7.75(4H, m), 8.10(1H, dd, J=1.6&4.4Hz), 11.15(1H, s). | 3050, 2970, 2220, 1575, 1435. |
| 21 | 1.48(9H, s), 7.18(1H, s), 7.32–7.38(1H, m), 7.42–7.72(5H, m), 8.27–8.32(1H, m). | 2975, 2550, 1570, 1455. |
| 22 | 1.37(9H, s), 7.17(1H, dd, J=4.4&8.0Hz), 7.35(1H, dd, J=1.6&8.0Hz), 7.56–7.68(4H, m), 8.11(1H, dd, J=1.6&4.4Hz), 11.27(1H, s). | 3060, 2970, 1610, 1580, 1440. |

TABLE 11

| Cpd. No. | ¹H-NMR(CDCl₃; TMS internal standard, ppm) | IR (KBr; cm⁻¹) |
|---|---|---|
| 23 | 1.50(9H, s), 7.19(1H, s), 7.35–7.57(3H, m), 7.76–7.81(1H, m), 8.21–8.32(3H, m). | 3060, 2970, 2580, 1570, 1530, 1345. |
| 24 | 1.38(9H, s), 7.19(1H, dd, J=4.4&8.4), 7.35–7.39(1H, m), 7.59–7.74(2H, m), 8.08–8.11(1H, m), 8.27–8.31(2H, m), 11.12(1H, s). | 3060, 2970, 1580, 1525, 1435, 1340. |
| 25 | *1.26(9H, s), 6.94(1H, d, J=8.6Hz), 7.31(1H, dd, J=6.4&8.4Hz), 7.35–7.41(2H, m), 7.61–7.66(1H, m), 7.86(1H, d, J=6.4Hz), 10.74(1H, s). | |
| 26 | 1.34(9H, s), 7.14–7.48(5H, m), 7.58–7.64(1H, m), 8.32–8.37(1H, m). | 3260, 2950, 1560. |

TABLE 11-continued

| Cpd. No. | $^1$H-NMR(CDCl$_3$; TMS internal standard, ppm) | IR (KBr; cm$^{-1}$) |
|---|---|---|
| 27 | 1.25(9H, s), 5.24(1H, s), 7.05(1H, dd, J=4.4&8.0Hz), 7.22–7.27(2H, m), 7.39–7.46(2H, m), 7.57–7.65(1H, m), 8.01(1H, dd, J=1.6&4.4Hz), 12.31(1H, s). | 3250, 2950, 1560, 1540. |
| 28 | *1.20(9H, s), 6.29(1H, s), 6.95(1H, d, J=8.6Hz), 7.21–7.45(5H, m), 7.97(1H, d, J=6.6Hz), 10.75(1H, s). | 3400, 2960, 1560. |
| 29 | *1.13(9H, s), 6.10(1H, s), 6.90(1H, d, J=8.6Hz), 7.14–7.22(1H, m), 7.33–7.55(4H, m), 7.72(1H, d, J=6.4Hz), 10.50(1H, s). | 3400, 2975, 2600, 1560. |

Experimental examples demonstrating the pharmacological effects of Compound [I] are shown below.

Experimental Example 1

Vasorelaxant effect on rat aorta preparations

Effects on contractions induced by tetraethyl ammonium chloride (TEA) and barium chloride (BaCl$_2$)

Method: Male Wistar rats (10 to 13 weeks old) were used. After exsanguination, the aorta was isolated. Aortic rings (5 mm long) were prepared and then suspended in a bath filled with oxygenated (95% O$_2$-5% CO$_2$) Krebs solution (36° C.). One end of each ring preparation was fixed and the other end was connected to a tension transducer (Nihon Kohden), and tension of the ring preparation was measured. After an equilibration period of one hour, TEA (30–45 mM) and BaCl$_2$ (0.3 mM) were added in the bath to produce vasoconstriction. After the contractions reached a steady state (after about 15 min.), each test compound was added and its relaxant effect was added and its relaxant effect was investigated.

Results: The results are given as percentage inhibition in Table 12. From these results, it is clear that the compound of this invention shows a vasorelaxant effect.

Experimental Example 2

Vasorelaxant effect on rat aorta preparations

Effect on constriction induced by potassium chloride (KCl)

Method: This experiment was performed using KCl (80 mM) instead of TEA and BaCl$_2$ used in Experimental Example 1. Apart from this, the procedures were substantially the same as in Experimental Example 1.

Results: The results are given as percentage inhibition in Table 13. From these results, it is clear that the vasorelaxant effect of the compound of this invention is due to the opening of potassium channels.

Experimental Example 3

Coronary blood flow-increasing effect in anesthetized dogs (administration into the coronary artery)

Method: After beagle dogs (10 to 12 kg) were anesthetized with pentobarbital, the chest was opened under artificial respiration. A bypass fitted with an electromagnetic flowmeter (Nihon Kohden) was prepared between the left coronary artery and the left carotid artery, and the coronary blood flow was measured. Each test compound was dissolved in 50% polyethylene glycol in physiological saline, 50% DMF in physiological saline or DMF for administration (30 μg/dog) into the coronary artery through the bypass.

Results: The greatest percentage change (% of basal flow) and duration (expressed as half-time (T$_{1/2}$) in which the effect is reduced to half) are shown in Table 14. From these results, it is clear that the compound of this invention increases the coronary blood flow.

Experimental Example 4

Antihypertensive effect in rats

Method: 23 to 27-week-old spontaneously hypertensive rats (SHR) or normotensive rats (Wistar-Kyoto rats (WKY)) were anesthetized with pentobarbital (60 mg/kg, i.p.). A polyethylene catheter filled with physiological saline containing 20% heparin was inserted into the left femoral artery and left in place. The other end of the catheter was tunneled subcutaneously to the back and fixed there. After one night, the animals were used in the experiment in the fasting state. Blood pressure was recorded on an ink-writing recorder through the arterial catheter via a pressure transducer. Blood pressure was estimated from flood pressure waves recorded on the recorder. After the blood pressure was stabilized, the test compounds (vehicle (0.5% methylcellulose, 2 mg/kg) or Compound 16 (0.3 mg/kg)) were administered orally. The subsequent changes in blood pressure and heart rate were observed at timed intervals.

Figure 1B:
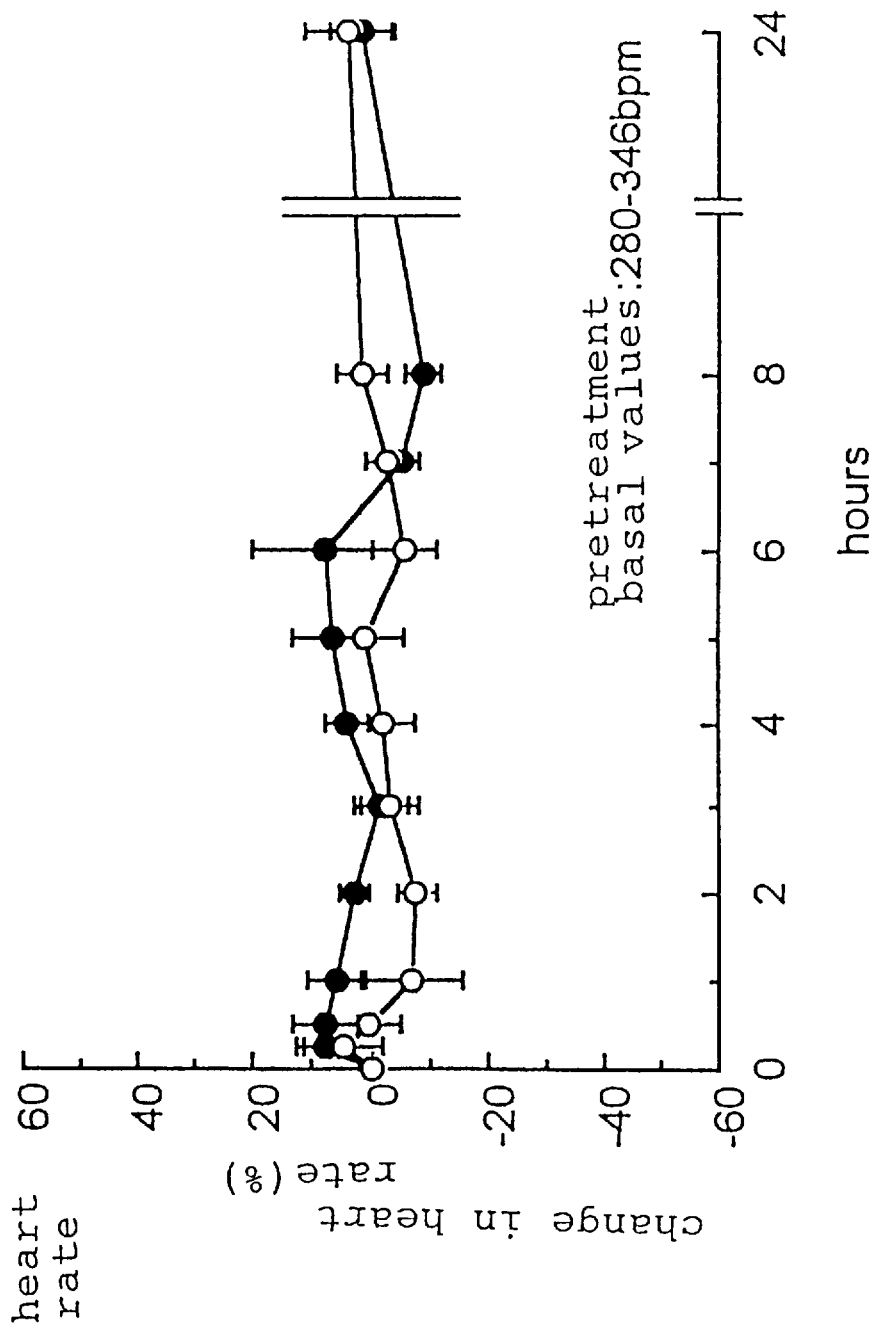

Results: The changes in blood pressure and heart rate after administration of the test compounds are given as % of pretreatment basal values (percentage changes) in FIGS. 1 and 2. All values are presented as means±standard error. As shown in FIG. 1, in SHR, Compound 16 had little effect on heart rate and exerted an antihypertensive effect of slow onset 2 hours after administration and long duration, with the greatest change of 18%. As shown in FIG. 2, Compound 16 at the same level had no effect on blood pressure or heart rate in WKY. From these results, it is clear that the compound of this invention shows useful and desirable blood blood pressure-lowering profiles.

TABLE 12

| | constriction inhibitory ratio (%) | | |
|---|---|---|---|
| Cpd. No. | 0.1 μM | 0.3 μM | 1 μM |
| 1 | 57 | 59 | |
| 3 | | 47 | 97 |
| 7 | | 2 | 72 |
| 11 | | 49 | 63 |
| 13 | | 21 | 53 |
| 16 | 87 | | |
| 21 | | 45 | 100 |
| 23 | 4 | 56 | 76 |
| 27 | 25 | 100 | |

TABLE 13

| | constriction inhibitory ratio (%) | | |
|---|---|---|---|
| Cpd. No. | 0.1 μM | 0.3 μM | 1 μM |
| 1 | 0 | 0 | |
| 3 | | 0 | 2 |
| 7 | | | 0 |
| 11 | | | 0 |

TABLE 13-continued

| Cpd. No. | constriction inhibitory ratio (%) | | |
| --- | --- | --- | --- |
| | 0.1 μM | 0.3 μM | 1 μM |
| 13 | | | 4 |
| 16 | 4 | | |
| 21 | | 1 | 8 |
| 23 | | 0 | 0 |
| 27 | 0 | 0 | |

TABLE 14

| Cpd. No. | greatest percentage change | duration ($T_{1/2}$, min) |
| --- | --- | --- |
| 1 | 133 | 6.7 |
| 3 | 155 | 24.4 |
| 7 | 71 | 18.6 |
| 11 | 66 | 30.5 |
| 16 | 136 | 43.5 |
| 23 | 134 | 5.3 |
| 27 | 77 | 74.6 |

We claim:

1. A compound of the formula

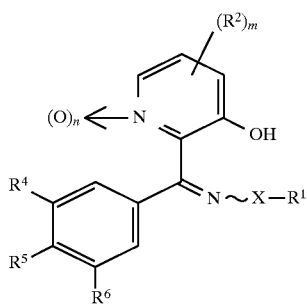

wherein $R^1$ is a branched $C_{3-8}$ alkyl group or a $C_{3-8}$ cycloalkyl group, each of which is optionally substituted with 1 to 3 groups selected from (i) a halogen atom, (ii) a halogeno $C_{1-4}$ alkyl group, (iii) a $C_{1-4}$ alkoxy group, (iv) a phenyl group which is optionally substituted with 1 to 3 groups selected from a $C_{1-4}$ alkyl group, a $C_{1-4}$ alkoxy group, a hydroxy group, a nitro group, a halogen atom, a halogeno $C_{1-4}$ alkyl group, a cyano group and a halogeno $C_{1-4}$ alkoxy group, (v) $CO_2R^7$ in which $R^7$ is a hydrogen atom or a $C_{1-4}$ alkyl group and (vi) $CH_2OR^8$ in which $R^8$ is a hydrogen atom or a $C_{1-4}$ alkyl group;

$R^2$ is a halogen atom, a $C_{1-4}$ alkyl group or a $C_{1-4}$ alkoxy group;

X is an oxygen atom;

$R^4$, $R^5$ and $R^6$ are independently (1) a hydrogen atom, (2) a halogen atom, (3) a cyano group, (4) a nitro group, (5) a $C_{1-4}$ acyl group, (6) a $C_{1-4}$ alkoxy group which is optionally substituted with halogen, (7) a $C_{1-4}$ alkyl group which is optionally substituted with halogen or (8) a mercapto group which is optionally substituted with a $C_{1-4}$ alkyl group;

m is 0 to 3; and n is 0 or 1;

provided that all of $R^4$, $R^5$ and $R^6$ are not hydrogen atoms, or a pharmaceutically acceptable salt thereof.

2. A compound of claim 1, wherein $R^4$, $R^5$ and $R^6$ are independently a hydrogen atom, a halogen atom, a cyano group, a nitro group or a halogeno-$C_{1-4}$ alkyl group.

3. A compound of claim 1, wherein $R^4$ and $R^5$ are a halogen atom and $R^6$ is a hydrogen atom.

4. A compound of claim 1, wherein $R^1$ is a branched $C_{3-8}$ alkyl group or a $C_{3-8}$ cycloalkyl group, each of which is optionally substituted with (i) halogen, (ii) $CO_2R^7$ in which $R^7$ is hydrogen or $C_{1-4}$ alkyl or (iii) $CH_2OR^8$ in which $R^8$ is hydrogen or $C_{1-4}$ alkyl.

5. A compound of claim 1, wherein $R^1$ is a $C_{3-8}$ alkyl group branched at α-position.

6. A compound of claim 1, wherein $R^1$ is a t-butyl group.

7. A compound of claim 1, wherein m is 0.

8. A compound of claim 1, wherein n is 0.

9. A compound of claim 1, which is a Z isomer.

10. A compound of claim 1, wherein $R^1$ is a branched $C_{3-8}$ alkyl group; X is an oxygen atom; $R^4$, $R^5$ and $R^6$ are independently a hydrogen atom, a halogen atom, a cyano group, a nitro group or a halogeno-$C_{1-4}$ alkyl group; m is 0; and n is 0 or 1.

11. A compound of claim 1, which is (Z)-2-[3-bromo-α-(t-butoxyimino)benzyl]-3-hydroxypyridine or a pharmaceutically acceptable salt thereof.

12. A compound of claim 1, which is (Z)-2-[α-(t-butoxyimino)-3,5-dichlorobenzyl]-3-hydroxypyridine or a pharmaceutically acceptable salt thereof.

13. A compound of claim 1, which is (Z)-2-[3-bromo-α-(t-butoxyimino)-4-fluorobenzyl]-3-hydroxypyridine or a pharmaceutically acceptable salt thereof.

14. A compound of claim 1, which is (Z)-2-[α-(t-butoxyimino)-3-trifluoromethylbenzyl]-3-hydroxypyridine or a pharmaceutically acceptable salt thereof.

15. A compound of claim 1, which is (Z)-2-[α-(t-butoxyimino)-3-nitrobenzyl]-3-hydroxypyridine or a pharmaceutically acceptable salt thereof.

16. A compound of claim 1, which is (Z)-2-[3-bromo-α-(t-butoxyimino)-4-fluorobenzyl]-3-hydroxypyridine N-oxide or a pharmaceutically acceptable salt thereof.

17. A pharmaceutical composition which comprises an effective amount of a compound of claim 1, in admixture with a pharmaceutically acceptable carrier, excipient or diluent.

18. A pharmaceutical composition for treating cardiovascular disease, which comprises an effective amount of a compound of claim 1, in admixture with a pharmaceutically acceptable carrier, excipient diluent.

19. A pharmaceutical composition of claim 18, wherein the cardiovascular disease is angina pectoris.

20. A pharmaceutical composition of claim 18, wherein the cardiovascular disease is hypertension.

21. A method for treating cardiovascular disease in a mammal in need thereof, which comprises administering an effective amount of a compound of claim 1 to said mammal.

22. A method of claim 21, wherein the cardiovascular disease is angina pectoris.

23. A method of claim 21, wherein the cardiovascular disease is hypertension.

24. A process for producing a compound of claim 1, which comprises reacting a compound of the formula

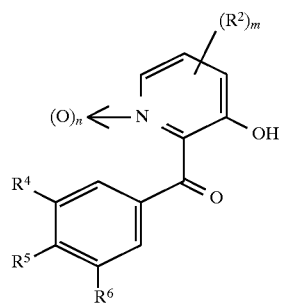
wherein the symbols are as defined in claim 1 or a salt thereof, with a compound of the formula
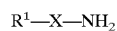
wherein the symbols are as defined in claim 1 or a salt thereof.
* * * * *